United States Patent
David

(10) Patent No.: US 7,014,705 B2
(45) Date of Patent: *Mar. 21, 2006

(54) MICROFLUIDIC DEVICE WITH DIFFUSION BETWEEN ADJACENT LUMENS

(75) Inventor: Peter R. David, Palo Alto, CA (US)

(73) Assignee: Takeda San Diego, Inc., San Diego, CA (US)

( * ) Notice: Subject to any disclaimer, the term of this patent is extended or adjusted under 35 U.S.C. 154(b) by 735 days.

This patent is subject to a terminal disclaimer.

(21) Appl. No.: 10/060,872

(22) Filed: Jan. 29, 2002

(65) Prior Publication Data

US 2003/0005877 A1 Jan. 9, 2003

Related U.S. Application Data

(63) Continuation-in-part of application No. 09/877,405, filed on Jun. 8, 2001.

(51) Int. Cl.
C30B 7/00 (2006.01)
C30B 29/38 (2006.01)

(52) U.S. Cl. .............................. 117/68; 117/69; 117/70; 117/201; 117/202; 117/927; 422/245.1; 23/295 R

(58) Field of Classification Search ................... 117/68, 117/69, 70, 201, 202, 206, 927; 422/245.1; 23/295 R
See application file for complete search history.

(56) References Cited

U.S. PATENT DOCUMENTS

| | | | |
|---|---|---|---|
| 4,908,112 A | 3/1990 | Pace | 204/299 |
| 5,132,012 A | 7/1992 | Miura et al. | 210/198.2 |
| 5,180,480 A | 1/1993 | Manz | 204/299 R |
| 5,296,114 A | 3/1994 | Manz | 204/180.1 |
| 5,485,270 A | 1/1996 | Freud et al. | 356/336 |
| 5,833,860 A | 11/1998 | Kopaciewicz et al. | |
| 6,220,075 B1 | 4/2001 | Papen et al. | |
| 6,267,935 B1 | 7/2001 | Hol et al. | 422/245.1 |
| 6,409,832 B1 | 6/2002 | Weigl et al. | 117/206 |
| 6,527,432 B1 | 3/2003 | Kellogg et al. | |
| 2002/0029814 A1 | 3/2002 | Unger et al. | |
| 2002/0137218 A1 | 9/2002 | Mian et al. | |
| 2002/0144736 A1 | 10/2002 | Unger et al. | |
| 2002/0145231 A1 | 10/2002 | Quake et al. | |
| 2002/0189529 A1 | 12/2002 | David et al. | |
| 2002/0195046 A1 | 12/2002 | David et al. | |
| 2002/0195048 A1 | 12/2002 | David | |
| 2002/0195050 A1 | 12/2002 | David | |
| 2003/0061687 A1 | 4/2003 | Hansen et al. | |

FOREIGN PATENT DOCUMENTS

| | | |
|---|---|---|
| WO | WO 93/06479 | 4/1993 |
| WO | WO 00/60345 | 10/2002 |

OTHER PUBLICATIONS

Sanjoh et al., "Spatiotemporal protien crystal growth studies using microfluidic silicon divices", Journal of Crystal Growth, vol. 196 (1999) pp. 691–702.*

Wilson, et al. "Control of Solvent Evaporation in Hen Egg White Lysozyme Crystallization," Journal of Crystal Growth, vol. 116, 1992, pp. 414–420.

US 2001/0011071 A1, Aug. 2, 2001, Kundsen et al., entitled "Derivatives of GLP–1 Analogs", 132 pages.

Van der Woerd, Mark, Lab–on–a–Chip Based Protein Crystallization, Presentation: NASA, Marshall Space Flight Center, Oct. 25, 2001 (27 pages).

* cited by examiner

Primary Examiner—Robert Kunemund
(74) Attorney, Agent, or Firm—David J. Weitz

(57) ABSTRACT

A microfluidic method is provided that comprises: delivering a first fluid to a first lumen of a microfluidic device and a second, different fluid to a second lumen of the microfluidic device, the first and second lumens sharing a common wall which allows for diffusion between the lumens over at least a portion of the length of the lumens; and having the first and second fluids diffuse between the first and second lumens.

34 Claims, 25 Drawing Sheets

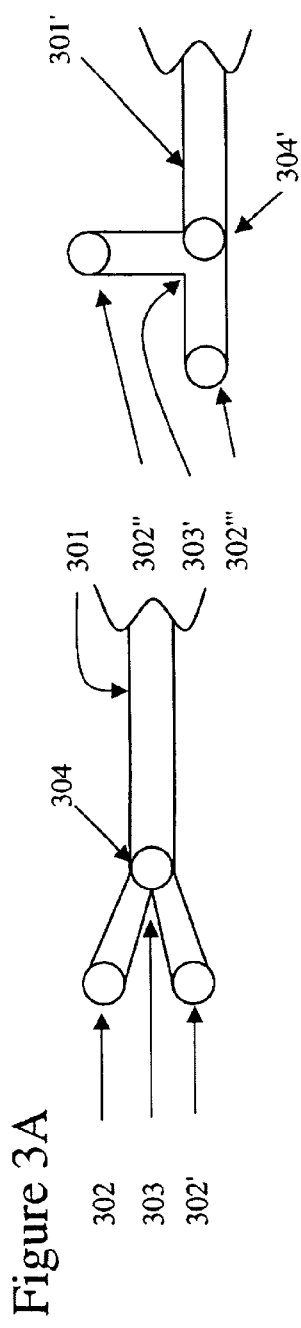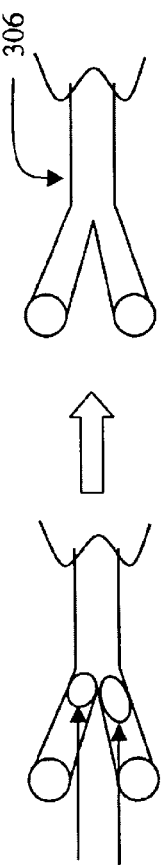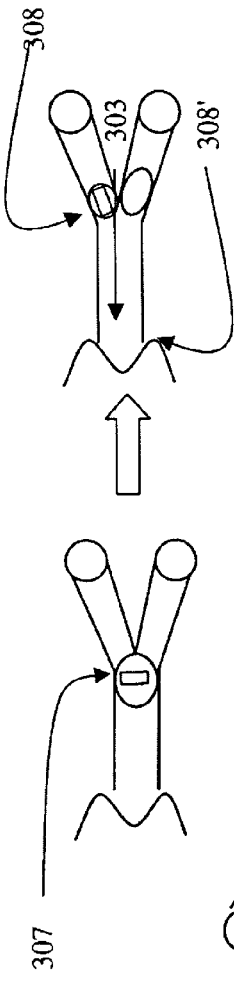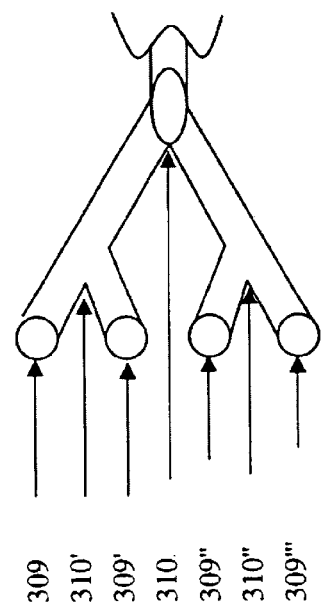
Figure 3A
Figure 3B
Figure 3C
Figure 3D

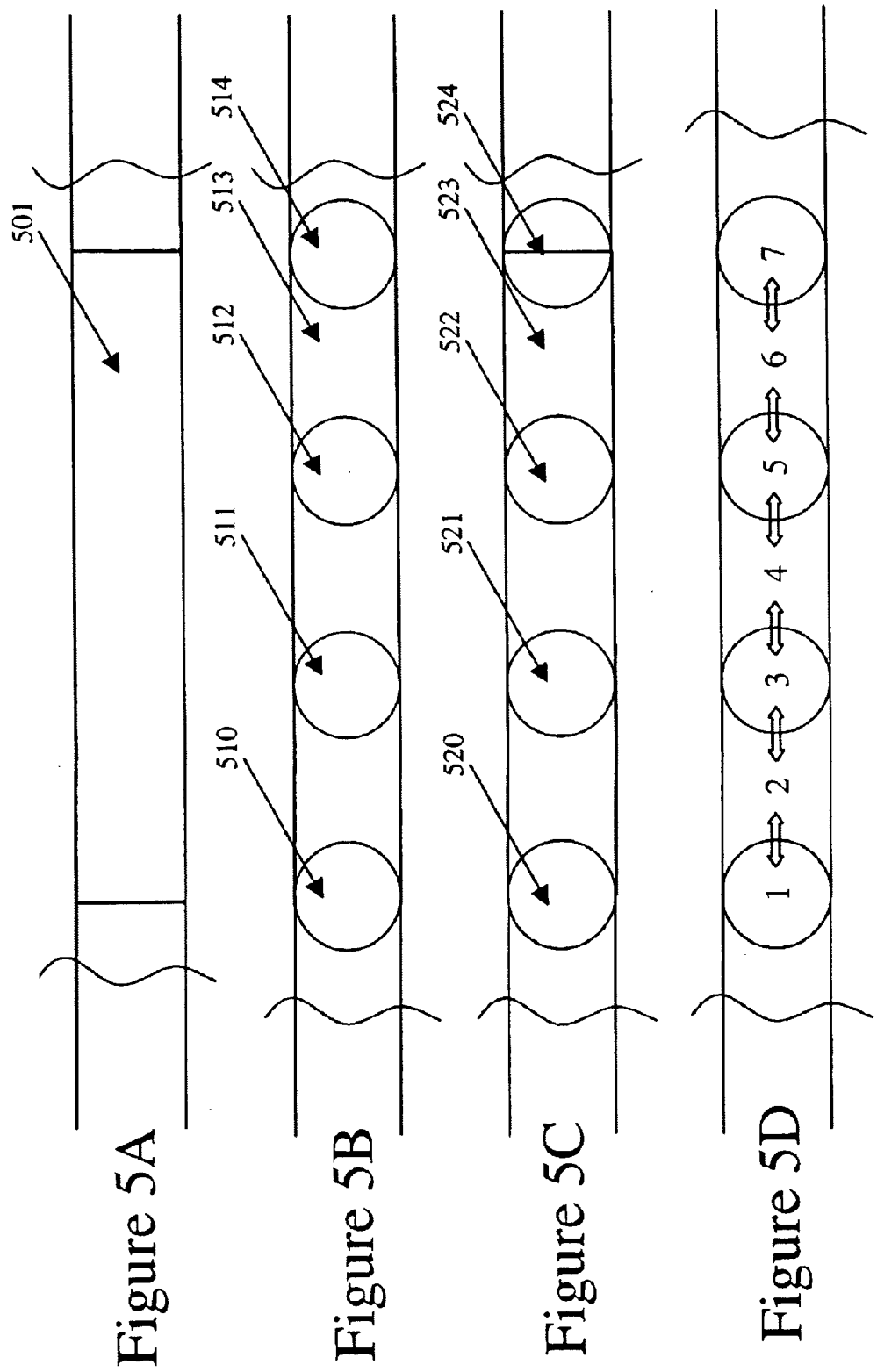

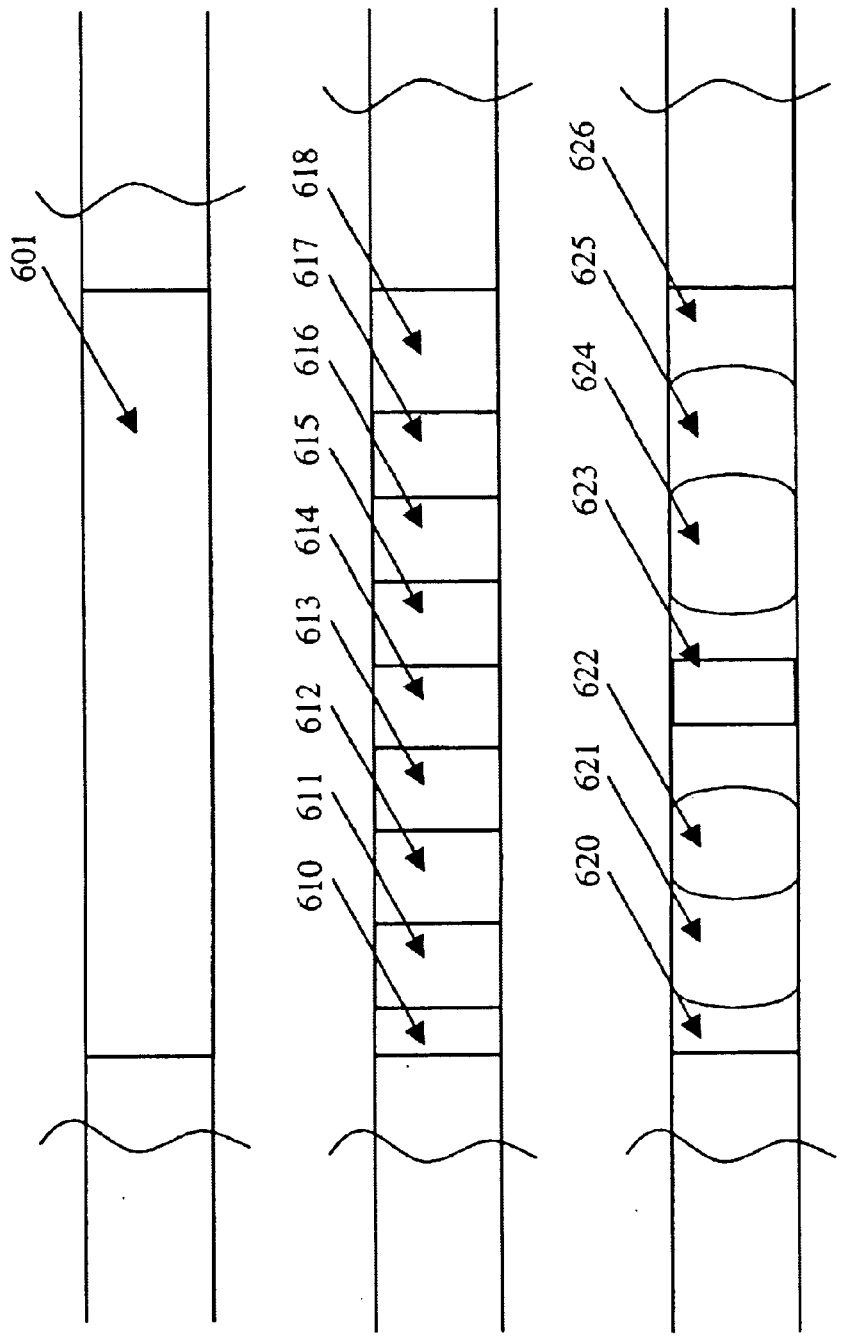

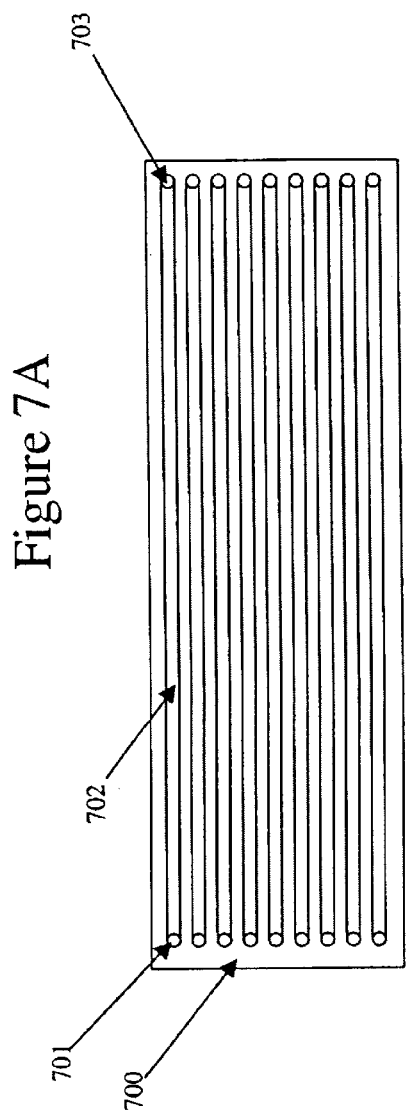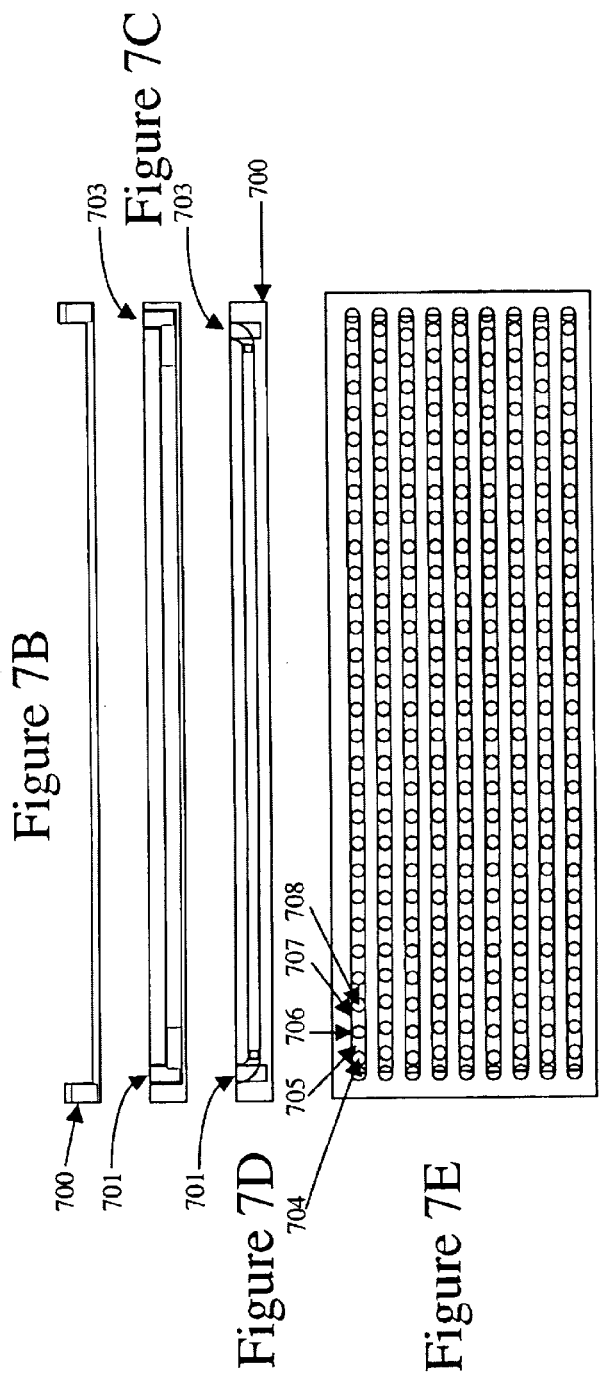

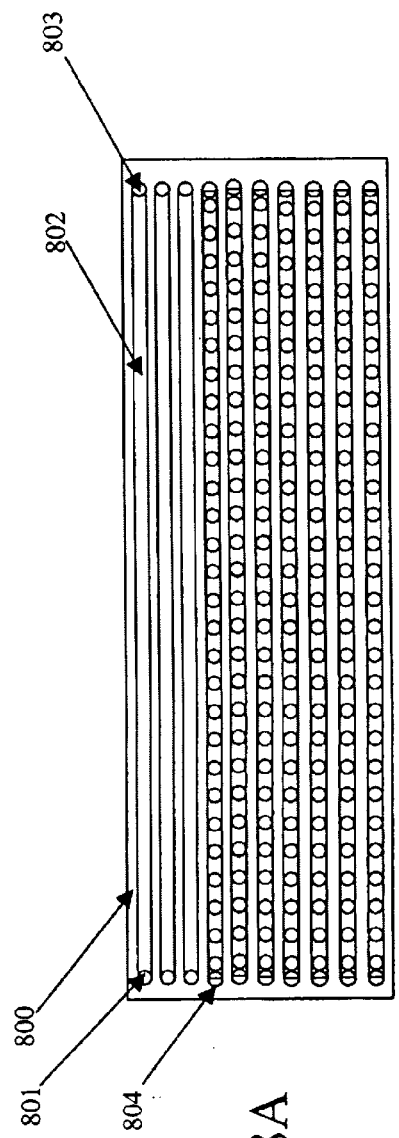
Figure 8A
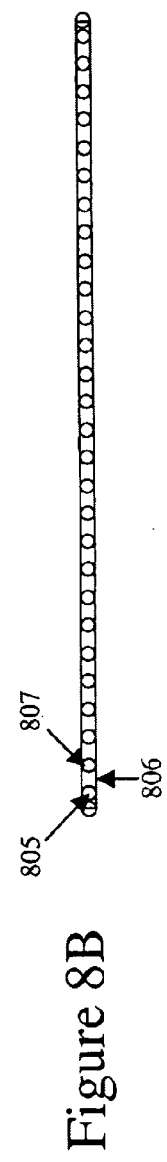
Figure 8B
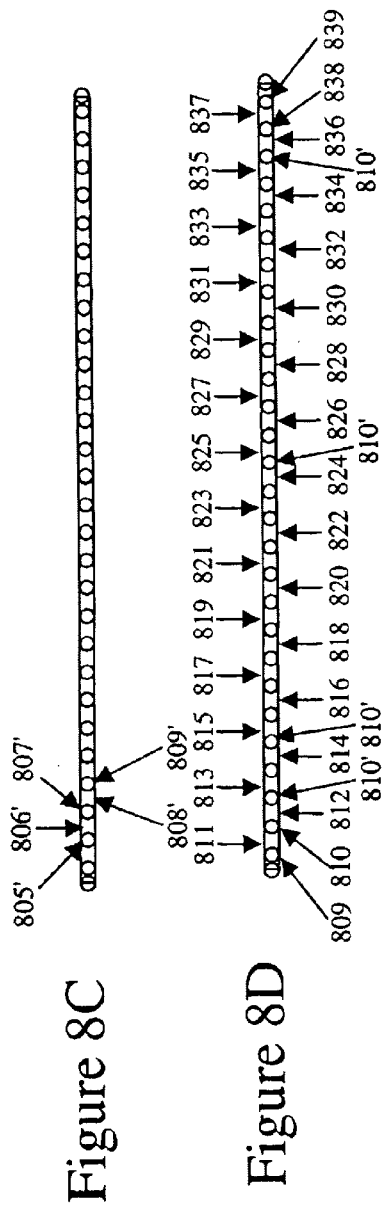
Figure 8C
Figure 8D

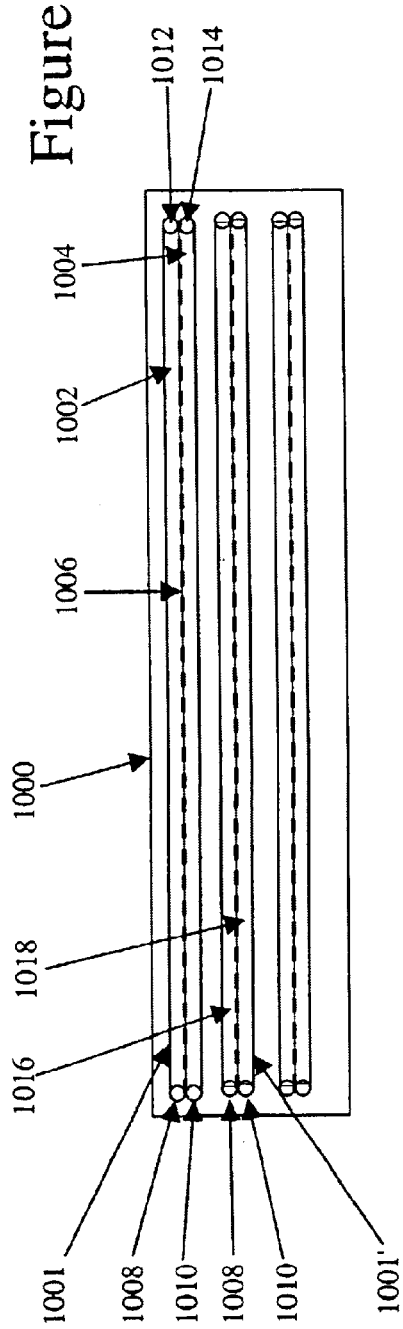
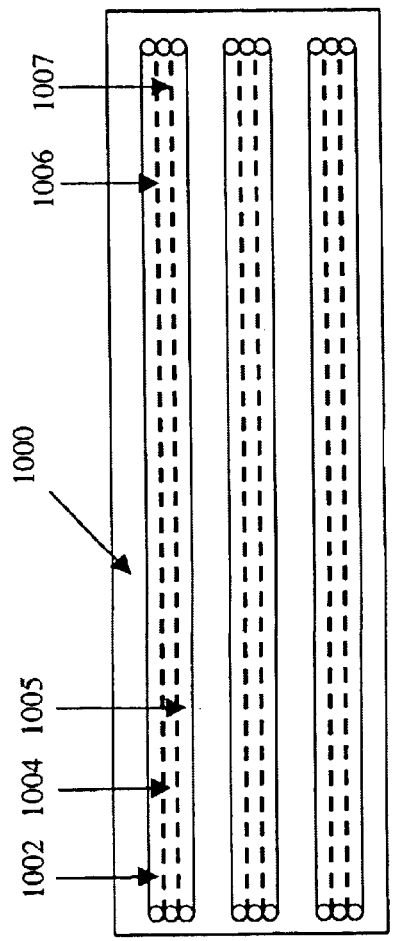

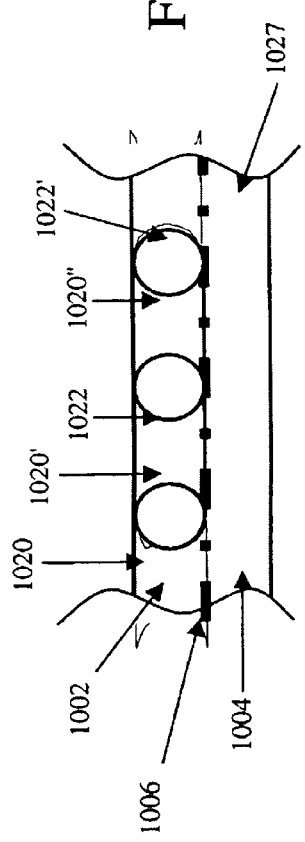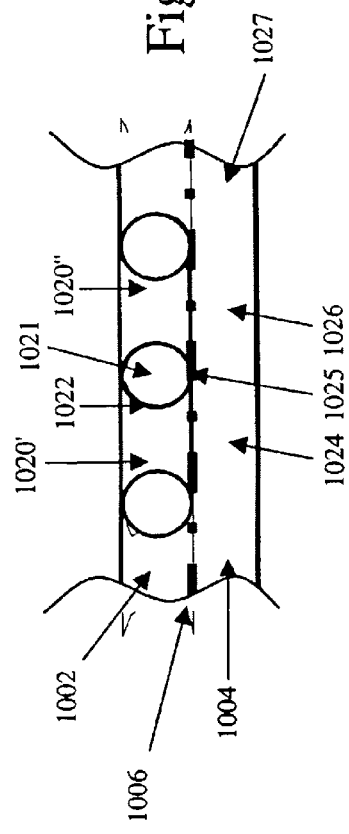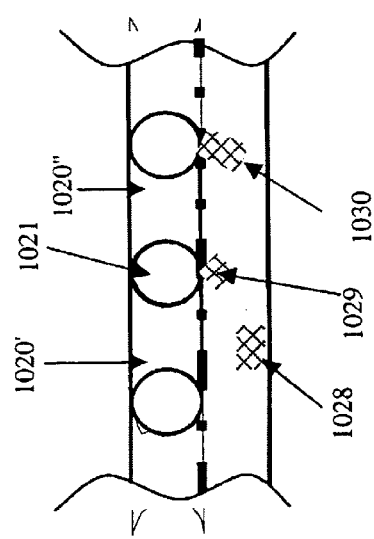

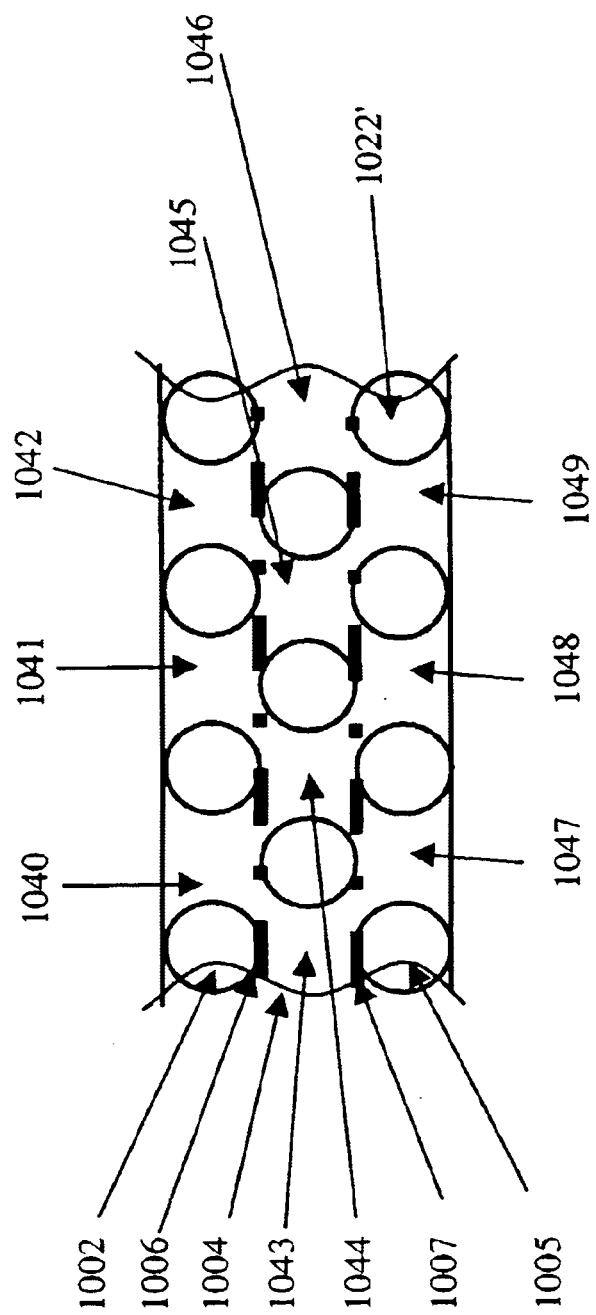

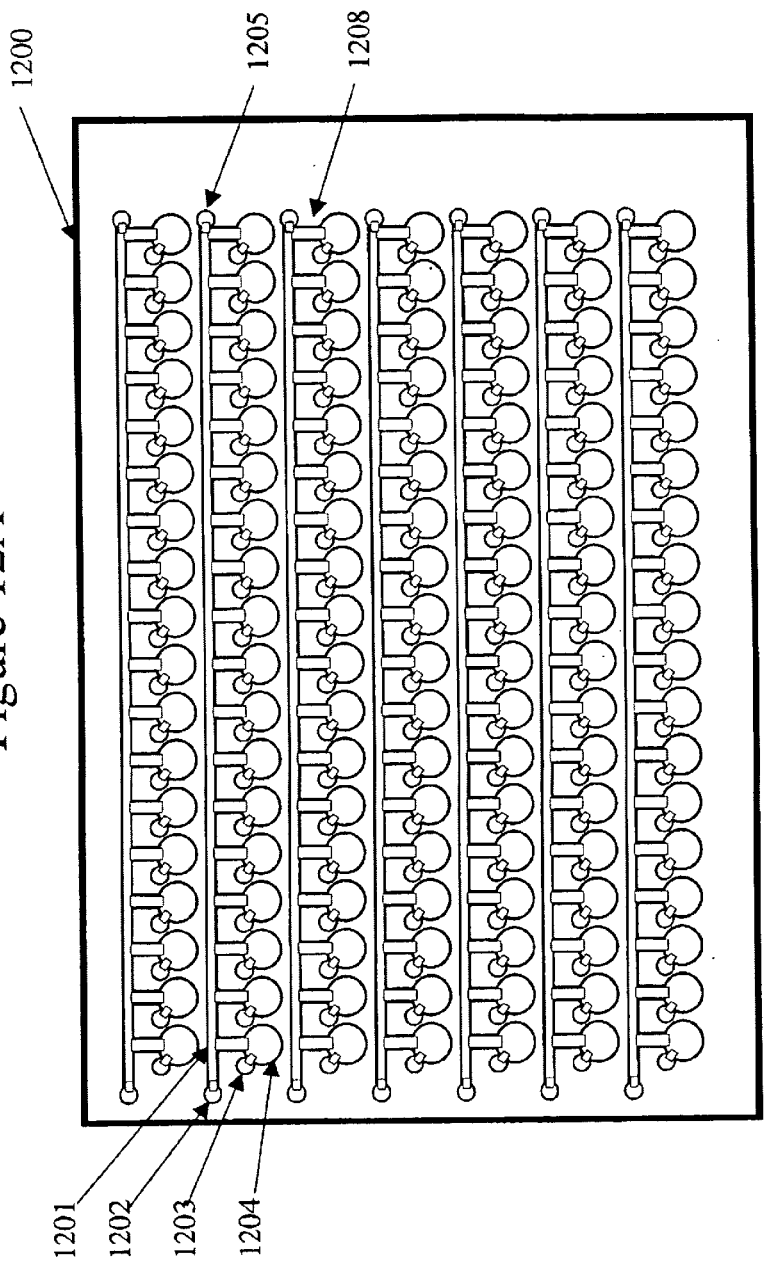
Figure 12A
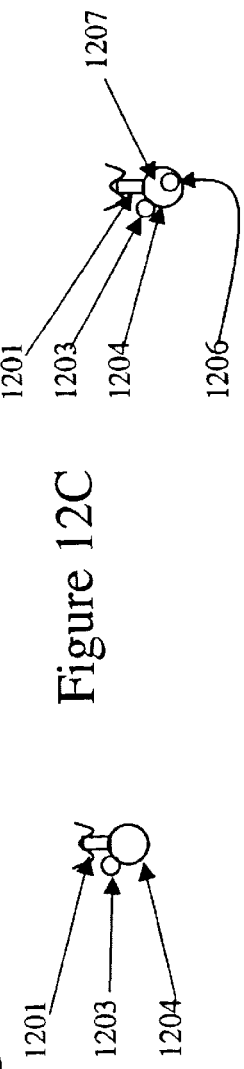
Figure 12B
Figure 12C

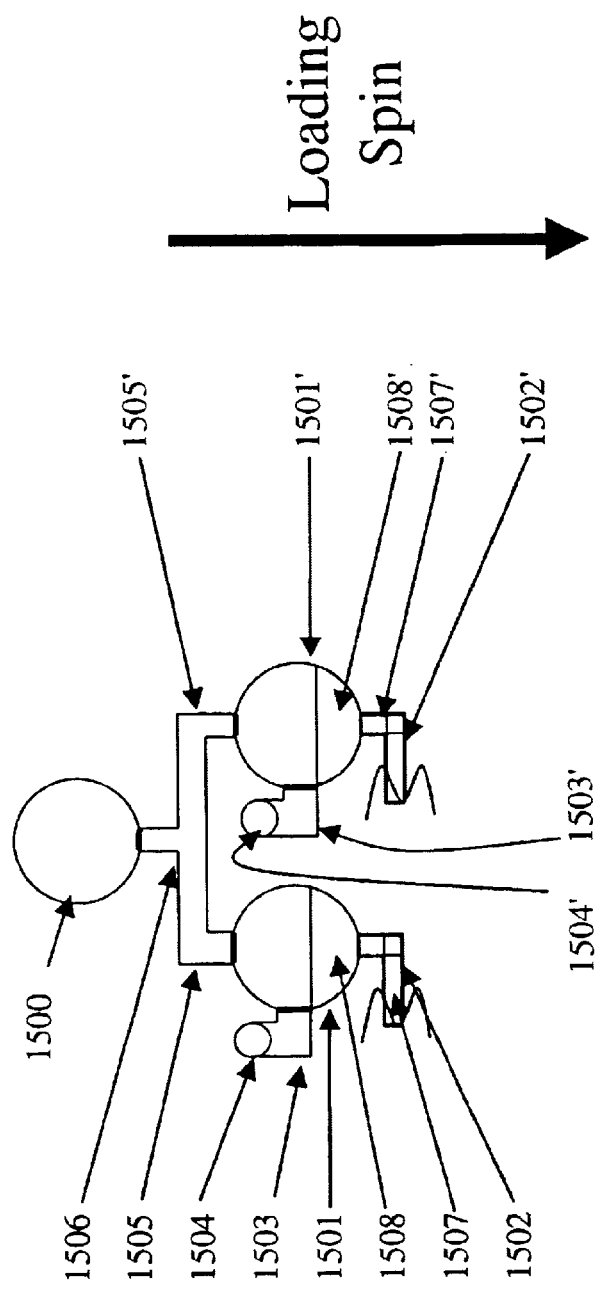

MICROFLUIDIC DEVICE WITH DIFFUSION BETWEEN ADJACENT LUMENS

RELATED APPLICATION

This application is a continuation in part of U.S. patent application Ser. No. 09/877,405 filed Jun. 8, 2001, which is incorporated herein by reference.

BACKGROUND OF THE INVENTION

1. Field of the Invention

The present invention relates to microfluidic devices and methods.

2. Description of Related Art

Traditional methods for crystal growth and crystallization are highly labor intensive and require significant quantities of material to evaluate and optimize crystal growth conditions. Examples of these methods include the free interface diffusion method (Salemme, F. R. (1972) Arch. Biochem. Biophys. 151:533–539), vapor diffusion in the hanging or sitting drop method (McPherson, A. (1982) Preparation and Analysis of Protein Crystals, John Wiley and Son, New York, pp 82–127), and liquid dialysis (Bailey, K. (1940) Nature 145:934–935).

Presently, the hanging drop method is the most commonly used method for growing macromolecular crystals from solution, especially for protein crystals. Generally, a droplet containing a protein solution is spotted on a cover slip and suspended in a sealed chamber that contains a reservoir with a higher concentration of precipitating agent. Over time, the solution in the droplet equilibrates with the reservoir by diffusing water vapor from the droplet, thereby slowly increasing the concentration of the protein and precipitating agent within the droplet, which in turn results in precipitation or crystallization of the protein.

The process of growing crystals with high diffraction quality is time-consuming and involves trial-and-error experiment on multiple solution variables such as pH, temperature, ionic strength, and specific concentrations of salts, organic additives, and detergents. In addition, the amount of highly purified protein is usually limited, multi-dimensional trials on these solution conditions are unrealistic, labor-intensive and costly.

A few automated crystallization systems have been developed based on the hanging drop methods, for example Cox, M. J. and Weber, P. C. (1987) J. Appl. Cryst. 20:366; and Ward, K. B. et al. (1988) J. Crystal Growth 90:325–339. More recently, systems for crystallizing proteins in submicroliter drop volumes have been described including those described in PCT Publication Nos. WO00/078445 and WO00/060345.

Existing crystallization, such as hanging drop, sitting drop, dialysis and other vapor diffusion methods have the limitation that the material for analysis and the crystallization medium are exposed to the environment for some time. As the volumes of materials decrease, the ratio of surface area to volume ratio varies as the inverse of the radius of the drop. This causes smaller volumes to be more susceptible to evaporation during the initial creation of the correct mixture and during the initial period after the volume has been set up. Typical hanging drop plates can have air volumes of 1.5 milliliters compared to a sample drop size of 3–10 microliters. Moreover, typical methods expose the sample drop to the environment for a duration of seconds to minutes. Small variability in the rate that samples are made can cause significant variations in the production of crystals. Small variations external environment also can cause significant variations in the production of crystals even if the rate that the samples are made is unchanged. Prior methods fail to reduce the problems of convection currents under 1 g such as those described in U.S. Pat No. 4,886,646, without the large expenditure of resources or in methods that complicate crystal analysis.

SUMMARY OF THE INVENTION

The present invention relates to various microfluidics devices, methods, and kits.

In one embodiment, a microfluidic device is provided that comprises: a card shaped substrate having first and second opposing faces; one or more microvolumes at least partially defined by a first face of the card shaped substrate; and one or more grooves at least partially defined by a second face of the card shaped substrate; wherein a lateral footprint of at least a portion of the one or more grooves overlaps with a lateral footprint of at least one of the one or more microvolumes.

Optionally, the one or more grooves are sufficiently deep relative to the second face of the substrate within the overlapping lateral footprint that when the portion of the microvolume within the overlapping lateral footprint comprises a crystallization sample and an x-ray beam traverses the card shaped substrate at the overlapping lateral footprint, the portion of the microvolume that the x-ray beam traverses contains at least half as many electrons as is contained in the substrate where the x-ray beam traverses. Optionally, the portion of the microvolume that the x-ray beam traverses contains at least as many electrons as is contained in the substrate where the x-ray beam traverses. Preferably, the portion of the microvolume that the x-ray beam traverses contains at least three, five, ten times or more times as many electrons as is contained in the substrate where the x-ray beam traverses.

Optionally, the one or more microvolumes comprise at least one lumen. In such an instance, the groove may have a longitudinal axis that is aligned with a longitudinal axis of the lumen adjacent the overlapping lateral footprint. The groove may also have a longitudinal axis that is perpendicular to a longitudinal axis of the lumen adjacent the overlapping lateral footprint.

In another embodiment, a microfluidic device is provided that comprises: a card shaped substrate having first and second opposing faces; a plurality of microvolumes at least partially defined by a first face of the card shaped substrate; and one or more grooves at least partially defined by a second face of the card shaped substrate; wherein a lateral footprint of at least a portion of the one or more grooves overlaps with lateral footprints of plurality of microvolumes.

In another embodiment, a method is provided for use with a microfluidic device, the method comprising: performing an experiment in a microfluidic device comprising a card shaped substrate having first and second opposing faces, one or more microvolumes at least partially defined by a first face of the card shaped substrate; and one or more grooves at least partially defined by a second face of the card shaped substrate; wherein a lateral footprint of at least a portion of the one or more grooves overlaps with a lateral footprint of at least one of the one or more microvolumes; and performing a spectroscopic analysis within the overlapping lateral footprint. Optionally, the microfluidic device comprises a card shaped substrate.

In another embodiment, a method is provided for use with a microfluidic device, the method comprising: performing an experiment in a microvolume of a microfluidic device; and performing a spectroscopic analysis using an x-ray beam that traverses the microfluidic device such that material within the microfluidic device that the x-ray beam traverses contains at least as many electrons as is otherwise traversed when the x-ray beam traverses the microfluidic device. Optionally, the material within the microfluidic device that the x-ray beam traverses contains at least three, five, ten times or more times as many electrons as is otherwise traversed when the x-ray beam traverses the microfluidic device.

In another embodiment, a method is provided for determining crystallization conditions for a material, the method comprising: taking a plurality of different crystallization samples in an enclosed microvolume, the plurality of crystallization samples comprising a material to be crystallized and crystallization conditions which vary among the plurality of crystallization samples; allowing crystals of the material to form in the plurality of crystallization samples; and identifying which of the plurality of crystallization samples comprise a precipitate, oil or a crystal of the material. One or more dividers may optionally be positioned between different crystallization samples in enclosed microvolume to separate adjacent crystallization samples.

In another embodiment, a method is provided for determining crystallization conditions for a material, the method comprising: taking a plurality of different crystallization samples in a plurality of enclosed microvolumes, each microvolume comprising one or more crystallization samples, the crystallization samples comprising a material to be crystallized and crystallization conditions that vary among the plurality of crystallization samples; allowing crystals of the material to form in plurality of crystallization samples; and identifying which of the plurality of crystallization samples comprise a precipitate, oil or a crystal of the material. One or more dividers may optionally be positioned between different crystallization samples in the enclosed microvolumes to separate adjacent crystallization samples.

In another embodiment, a method is provided for determining crystallization conditions for a material, the method comprising: taking a microfluidic device comprising one or more lumens having microvolume dimensions and a plurality of different crystallization samples within the one or more lumens, the plurality of crystallization samples comprising a material to be crystallized and crystallization conditions that vary among the plurality of crystallization samples; transporting the plurality of different crystallization samples within the lumens; and identifying a precipitate or crystal formed in the one or more lumens. Transporting the plurality of different crystallization samples within the one or more lumens may be performed by a variety of different methods. For example, transporting may be performed by a method selected from the group consisting of electrophoresis, electroosmotic flow and physical pumping. In one variation, transporting is performed by electrokinetic material transport.

In a variation according to this embodiment, at least one of the lumens optionally comprises a plurality of different crystallization samples. One or more dividers may be positioned between different crystallization samples in at least one of the lumens to separate adjacent crystallization samples.

Also according to this embodiment, the method may further comprise forming the plurality of different crystallization samples within the one or more lumens. The plurality of crystallization samples may be comprised in a single lumen or a plurality of lumens.

In another embodiment, a method is provided for determining crystallization conditions for a material, the method comprising: taking a microfluidic device comprising one or more lumens having microvolume dimensions and a plurality of different crystallization samples within the one or more lumens, the plurality of crystallization samples comprising a material to be crystallized and crystallization conditions that vary among the plurality of crystallization samples; transporting the plurality of different crystallization samples within the one or more lumens; and identifying a precipitate or crystal formed in the one or more lumens; and performing a spectroscopic analysis on the identified precipitate or crystal while within the lumen.

The method may optionally further include forming the plurality of different crystallization samples within the one or more lumens. The plurality of crystallization samples may be comprised in a single lumen or multiple lumens.

In another embodiment, a microfluidic method is provided comprising: delivering a first fluid to a first lumen of a microfluidic device and a second, different fluid to a second lumen of the microfluidic device, the first and second lumens sharing a common wall that allows for diffusion between the lumens over at least a portion of the length of the lumens; and having the first and second fluids diffuse between the first and second lumens.

In one variation according to this method, a composition of at least one of the first and second fluids is varied so that the composition of at least one of the first and second fluids varies along a length of the lumen.

In another variation according to this method, the composition of at least one of the first and second fluids varies over time as it is delivered to the lumen so that the fluid forms a gradient with regard to a concentration of at least one component of the fluid that changes along a length of the lumen.

In another variation according to this method, the microfluidic device comprises a plurality of first and second lumens, the method comprising delivering first and second fluids to each of the plurality of first and second lumens.

In yet another variation according to this method, the same first and second fluids are delivered to each of the plurality of first and second lumens.

In yet another variation according to this method, different first and second fluids are delivered to the plurality of first and second lumens.

It is noted that the first and second fluids may have a same or different flow rate within the lumen. It is also noted that the first and second fluids may each optionally comprise more than one different fluid flow. The first and second fluids may also each optionally comprise dividers that separate the fluid into a plurality of aliquots separated by the dividers.

In another variation according to this method, the method optionally further comprises delivering a third fluid to a third lumen which shares a common wall with at least one of the first and second lumens, the common wall allowing for diffusion between the third lumen and the first or second lumen over at least a portion of the length of the lumens.

In another embodiment, a microfluidic device is provided that comprises: a substrate; a first lumen at least partially defined by the substrate; and a second lumen; wherein the first and second lumens share a common wall with each other that allows for diffusion between the two lumens over at least a portion of the length of the two lumens. The common wall may optionally comprise a membrane, gel, frit, or matrix that allows for diffusion between the two lumens.

Also according to this embodiment, the device may further comprise a third lumen, the third lumen sharing a common wall with at least one of the first and second lumens so as to allow for diffusion between the lumens over at least a portion of the length of the lumens.

In another embodiment, a microfluidic device is provided that comprises: a substrate; a plurality of sets of lumens, each set comprising a first lumen at least partially defined by the substrate, and a second lumen, wherein the first and second lumens share a common wall with each other that allows for diffusion between the two lumens over at least a portion of the length of the two lumens. The common wall may optionally comprise a membrane, gel, frit, or matrix that allows for diffusion between the two lumens.

According to this embodiment, the device may further comprise a third lumen, the third lumen sharing a common wall with at least one of the first and second lumens so as to allow for diffusion between the lumens over at least a portion of the length of the lumens.

Also according to this embodiment, the device may optionally comprise at least 4, 8, 12, 24, 96, 200, 1000 or more sets of lumens.

A variety of different devices and methods are also provided that use centrifugal force to cause fluid movement within a microfluidic device.

In one embodiment, a microfluidic method is provided that comprises: taking a microfluidic device comprising a plurality of microvolumes; and causing movement of material in a same manner within the plurality of microvolumes by applying centrifugal forces to the material.

In another embodiment, a microfluidic method is provided that comprises: taking a plurality of microfluidic devices, each device comprising a plurality of microvolumes; and causing movement of material in a same manner within the plurality of microvolumes of the plurality of devices by applying centrifugal forces to the material. Optionally, a same centrifugal force is applied to each of the plurality of devices.

In a variation, the plurality of microfluidic devices may be stacked relative to each other when the centrifugal forces are applied. The plurality of microfluidic devices may also be positioned about a rotational axis about which the plurality of microfluidic devices are rotated to apply the centrifugal forces.

In another embodiment, a microfluidic method is provided that comprises: taking a microfluidic device comprising a plurality of microvolumes; and physically moving the device so as to effect a same movement of material within the plurality of microvolumes. Physically moving the device preferably causes centrifugal force to be applied, for example, by rotation of the device about an axis.

According to this embodiment, the material moved in each of the plurality of microvolumes by movement of the device preferably has a same quantity.

In another embodiment, a microfluidic method is provided that comprises: taking a microfluidic device comprising a plurality of microvolumes; and accelerating or decelerating a motion of the device so as to effect a same movement of material within the plurality of microvolumes. According to this embodiment, the motion of the device is optionally a rotation of the device. In such instances, acceleration or deceleration may be caused by a change in a rate of rotation of the device.

In another embodiment, a microfluidic device is provided that comprises: a substrate; and a plurality of microvolumes at least partially defined by the substrate, each microvolume comprising a first submicrovolume and a second submicrovolume that is in fluid communication with the first submicrovolume when the device is rotated, the plurality of microvolumes being arranged in the device such that fluid in the first submicrovolumes of multiple of the microvolumes are transported to second submicrovolumes of the associated microvolumes when the device is rotated.

According to this embodiment, the device may be designed so that at least 4, 8, 12, 36, 96, 200, 1000 or more of the microvolumes are transported to second submicrovolumes of the associated microvolumes when the device is rotated.

Also according to this embodiment, the device may be designed so that the volume of fluid delivered from the first submicrovolume to the second submicrovolume of a given microvolume upon rotation of the device is within 50%, 25%, 10%, 5%, 2%, 1% or less of the volume of fluid delivered from the first submicrovolumes to the second submicrovolumes of any other microvolumes when a same volume of fluid is added to the first submicrovolumes.

In another embodiment, a microfluidic method is provided that comprises: taking a microfluidic device comprising a substrate, and a plurality of microvolumes at least partially defined by the substrate, each microvolume comprising a first submicrovolume and a second submicrovolume where the first submicrovolume and second microvolume are in fluid communication with each other when the device is rotated; adding fluid to a plurality of the first submicrovolumes; and rotating the device to cause fluid from the plurality of first submicrovolumes to be transferred to the second submicrovolumes in fluid communication with the first submicrovolumes.

According to this embodiment, the device may be designed so that at least 4, 8, 12, 24, 96, 200, 1000 or more of the microvolumes are transported to second submicrovolumes of the associated microvolumes when the device is rotated.

Also according to this embodiment, the device may be designed so that the volume of fluid delivered from the first submicrovolume to the second submicrovolume of a given microvolume upon rotation of the device is within 50%, 25%, 10%, 5%, 2%, 1% or less of the volume of fluid delivered from the first submicrovolumes to the second submicrovolumes of any other microvolumes when a same volume of fluid is added to the first submicrovolumes.

Also according to this embodiment, the method may be performed as part of performing an array crystallization trial. The array crystallization trial may involve the crystallization of a variety of different materials including various biomolecules such as proteins.

In another embodiment, a microfluidic method is provided that comprises: taking a plurality of microfluidic devices, each comprising a substrate, and a plurality of microvolumes at least partially defined by the substrate, each sample microvolume comprising a first submicrovolume and a second submicrovolume where the first submicrovolume and second submicrovolume are in fluid communication with each other when the device is rotated; adding fluid to a plurality of the first submicrovolumes in the plurality of microfluidic devices; and rotating the plurality of microfluidic devices at the same time to cause fluid from the plurality of first submicrovolumes to be transferred to the second submicrovolumes in fluid communication with the first submicrovolumes.

According to this embodiment, the plurality of microfluidic devices may optionally be stacked relative to each other during rotation. The plurality of microfluidic devices may also be positioned about a rotational axis about which the plurality of microfluidic devices are rotated. In one variation, the rotational axis about which the plurality of microfluidic devices are rotated is positioned within the lateral footprints of the plurality of microfluidic devices. In another variation, the rotational axis about which the plurality of microfluidic devices are rotated is positioned outside of the lateral footprints of the plurality of microfluidic devices.

In yet another embodiment, a microfluidic device is provided that comprises: a substrate shaped so as to provide the device with an axis of rotation about which the device may be rotated; and a plurality of microvolumes at least partially defined by the substrate, each microvolume comprising a first submicrovolume and a second submicrovolume that is in fluid communication with the first submicrovolume when the device is rotated, the plurality of microvolumes being arranged in the device such that fluid in the first submicrovolumes of multiple of the microvolumes are transported to the second submicrovolumes of the associated microvolumes when the device is rotated about the rotational axis. Optionally, the second microvolumes are lumens.

The device may optionally comprise a mechanism that facilitates the device being rotated about the rotational axis. For example, the substrate may define a groove or hole at the rotational axis that facilitates the device being rotated about the rotational axis. Optionally, a center of mass of the device is at the rotational axis and the substrate defines a groove or hole at the rotational axis that facilitates the device being rotated about the rotational axis. In one variation, the device is disc shaped, the substrate defining a groove or hole at the rotational axis of the disc that facilitates the device being rotated about the rotational axis.

Also according to this embodiment, the method may be performed as part of performing an array crystallization trial. The array crystallization trial may involve the crystallization of a variety of different materials including various biomolecules such as proteins, In another embodiment, a microfluidic method is provided that comprises: taking a microfluidic device comprising a substrate, and a plurality of microvolumes at least partially defined by the substrate, each microvolume comprising a first and a second submicrovolume where the first and second submicrovolumes are in fluid communication with each other when the device is rotated about a rotational axis of the device; adding fluid to a plurality of the first submicrovolumes; and rotating the device about the rotational axis of the device to cause fluid in the first submicrovolumes to be transferred to the second submicrovolumes.

Also according to this embodiment, the method may be performed as part of performing an array crystallization trial. The array crystallization trial may involve the crystallization of a variety of different materials including various biomolecules such as proteins.

In another embodiment, a microfluidic device is provided that comprises: a substrate; one or more microvolumes at least partially defined by the substrate, each microvolume comprising a first submicrovolume, a second submicrovolume where fluid in the first submicrovolume is transported to the second submicrovolume when the device is rotated about a first rotational axis, and a third submicrovolume where fluid in the first submicrovolume is transported to the third submicrovolume when the device is rotated about a second, different rotational axis. The device itself include features to facilitate the rotation of the device about one or more rotational axes. The device may alternative be rotated about one or more rotational axes by the use of an external fixture.

In another embodiment, a microfluidic device comprising: a substrate; one or more microvolumes extending along a plane of the substrate, each microvolume comprising a first submicrovolume, a second submicrovolume where fluid in the first submicrovolume is transported to the second submicrovolume when the device is rotated about a first rotational axis that is positioned further away from the second submicrovolume than the first submicrovolume, and a third submicrovolume where fluid in the first submicrovolume is transported to the third submicrovolume when the device is rotated about a second, different rotational axis that is positioned further away from the third submicrovolume than the first submicrovolume. Optionally, the substrate is card shaped. In such instances, the one or more microvolumes may optionally extend along a surface of the card shaped substrate.

In another embodiment, a microfluidic method is provided that comprises: taking a microfluidic device comprising a substrate and a plurality of microvolumes at least partially defined by the substrate, each microvolume comprising an first submicrovolume, a second submicrovolume where fluid in the first submicrovolume is transported to the second submicrovolume when the device is rotated about a first rotational axis, and a third submicrovolume where fluid in the first submicrovolume is transported to the third submicrovolume when the device is rotated about a second, different rotational axis; adding fluid to the first submicrovolumes of the microvolumes; and in any order rotating the device about the first and second rotational axes to cause fluid from the first submicrovolumes to be transferred to the second and third submicrovolumes.

It is noted that the method may be performed as part of performing an array crystallization trial. The array crystallization trial may involve the crystallization of a variety of different materials including various biomolecules such as proteins.

In another embodiment, a microfluidic device is provided that comprises: a substrate; and a plurality of microvolumes at least partially defined by the substrate, each microvolume comprising a first submicrovolume and a second submicrovolume in fluid communication with the first submicrovolume when the device is rotated about a first rotational axis, wherein rotation of the device about the first rotational axis causes a fixed volume to be transported to each of the second submicrovolumes.

According to this embodiment, the plurality of microvolumes may optionally further comprise one or more outlet submicrovolumes in fluid communication with the first submicrovolume.

Also according to this embodiment, the plurality of microvolumes may optionally further comprise one or more outlet submicrovolumes where fluid in the first submicrovolume not transported to the second submicrovolume when the device is rotated about a first rotational axis is transported to one or more one or more outlet submicrovolumes when the device is rotated about a second, different rotational axis.

In another embodiment, a microfluidic device is provided that comprises: a substrate; a first microvolume at least partially defined by the substrate comprising a first submicrovolume; a second submicrovolume where fluid in the first submicrovolume is transported to the second submicrovolume when the device is rotated about a first rotational axis; and a second microvolume at least partially defined by the substrate comprising a third submicrovolume; a fourth submicrovolume where fluid in the third submicrovolume is transported to the fourth submicrovolume when the device is rotated about the first rotational axis; and wherein fluid in the second and fourth submicrovolumes are transported to a fifth submicrovolume where the second and fourth submicrovolumes are mixed when the device is rotated about a second, different rotational axis.

According to this embodiment, the fifth submicrovolume may optionally be in fluid communication with the second and fourth submicrovolumes via the first and third submicrovolumes respectively.

Also according to this embodiment, the device may further comprise one or more outlet submicrovolumes in fluid communication with the first and third submicrovolumes.

Also according to this embodiment, the device may further comprise one or more outlet submicrovolumes in fluid communication with the first and second submicrovolumes where fluid in the first and third submicrovolumes not transported to the second and fourth submicrovolumes when the device is rotated about the first rotational axis is transported to one or more one or more outlet submicrovolumes when the device is rotated about a third, different rotational axis.

Also according to this embodiment, the device may further comprise at least 4, 8, 12, 24, 96, 200, 1000, or more pairs of first and second microvolumes.

Also according to this embodiment, the device may be designed such that the volume of fluid transported to any given second submicrovolume does not deviate from the volume of fluid transported to another second submicrovolume by more than 50%, 25%, 10%, 5%, 2%, 1% or less.

The device may also optionally be designed so that any of the following conditions are satisfied: the first rotational axis is positioned further away from the second and fourth submicrovolumes than the first and third submicrovolumes; the first rotational axis about which the microfluidic device is designed to be rotated is positioned within a lateral footprint of the microfluidic device; and the first rotational axis about which the microfluidic device is designed to be rotated is positioned outside of a lateral footprint of the microfluidic device.

In yet another embodiment, a microfluidic method is provided that comprises: taking a microfluidic device comprising a substrate, and a plurality of microvolumes at least partially defined by the substrate, each microvolume comprising a first submicrovolume and a second submicrovolume in fluid communication with the first submicrovolume; adding fluids to the first submicrovolumes; and applying a centrifugal force to the device to cause a same volume of fluid to be transported to the second microvolumes from the first submicrovolumes.

Optionally, the microvolumes may further comprise an outlet submicrovolume in fluid communication with the first submicrovolumes. In such instances, the method may further comprise transporting fluid in the first submicrovolume to the outlet submicrovolume that was not transported to the second submicrovolume when the centrifugal force was applied. The method may also further comprise transporting fluid in the first submicrovolume to the outlet submicrovolume that was not transported to the second submicrovolume when the device is rotated about a first rotational axis by rotating the device about a second, different rotational axis.

Also according to the embodiment, the device may be designed such that the volume of fluid transported to any given second submicrovolume does not deviate from the volume of fluid transported to another second submicrovolume by more than 50%, 25%, 10%, 5%, 2%, 1% or less.

In another embodiment, a microfluidic method is provided that comprises: taking a microfluidic device comprising a substrate, a first microvolume at least partially defined by the substrate comprising a first submicrovolume and a second submicrovolume where fluid in the first submicrovolume is transported to the second submicrovolume when the device is rotated about a first rotational axis, and a second microvolume at least partially defined by the substrate comprising a third submicrovolume and a fourth submicrovolume where fluid in the third submicrovolume is transported to the fourth submicrovolume when the device is rotated about the first rotational axis, the microvolumes further comprising a fifth submicrovolume where fluid in the second and fourth submicrovolumes are mixed when the device is rotated about a second, different rotational axis; adding a first fluid to the first submicrovolume and a second fluid to the third submicrovolume; rotating the device about the first rotational axis to transport the first and second fluids to the second and fourth submicrovolumes; and rotating the device about the second rotational axis to transport the first and second fluids from the second and fourth submicrovolumes to the fifth submicrovolume.

In one variation, the fifth submicrovolume is in fluid communication with the second and fourth submicrovolumes via the first and third submicrovolumes respectively.

Optionally, the method further comprises removing fluid from the first and third submicrovolumes that is not transported to the second and fourth submicrovolumes prior to rotating the device about the second rotational axis.

Also according to the embodiment, the device may comprise a plurality of pairs of first and second microvolumes and the volume of fluid transported to any given second submicrovolume does not deviate from the volume of fluid transported to another second submicrovolume by more than 50%, 25%, 10%, 5%, 2%, 1% or less.

In another embodiment, a microfluidic method is provided that comprises: delivering first and second fluids to a lumen of a microfluidic device such that the first and second fluids flow adjacent to each other within the lumen without mixing except for diffusion at an interface between the first and second fluids, wherein the first fluid is different than the second fluid.

According to this embodiment, the composition of at least one of the first and second fluids is optionally varied over time as it is delivered to the lumen so that the fluid forms a gradient with regard to a concentration of at least one component of the fluid that changes along a length of the lumen.

According to this embodiment, the microfluidic device may comprise a plurality of lumens, the method optionally comprising delivering first and second fluids to each of the plurality of lumens.

According to this embodiment, the same first and second fluids may be delivered to each of the plurality of lumens. Alternatively, different first and second fluids are delivered to the different lumens of the plurality of lumens. The first and second fluids may also have a same or different flow rate within the lumen.

Also according to this embodiment, the first and second fluids may be combined to form different crystallization conditions for crystallizing a molecule such as a protein.

In another embodiment, a microfluidic method is provided that comprises: delivering first and second fluids to a lumen of a microfluidic device such that the first and second fluids flow adjacent to each other within the lumen without mixing except for diffusion at an interface between the first and second fluids, wherein the first fluid is different than the second fluid and a composition of at least one of the first and second fluids delivered to the lumen is varied so that the composition of at least one of the first and second fluids within the lumen varies along a length of the lumen.

In yet another embodiment, a microfluidic method is provided that comprises: delivering first, second and third fluids to a lumen of a microfluidic device such that the first, second and third fluids flow adjacent to each other within the lumen without mixing except for diffusion at an interface between the first, second and third fluids, wherein the first, second and third fluids are different than each other and a composition of at least one of the first, second and third fluids delivered to the lumen is varied so that the composition of at least one of the first, second, and third fluids within the lumen varies along a length of the lumen.

According to this embodiment, the composition of at least one of the first, second and third fluids may be varied over time as it is delivered to the lumen so that the fluid forms a gradient with regard to a concentration of at least one component of the fluid that changes along a length of the lumen.

Also according to this embodiment, the microfluidic device may comprise a plurality of lumens, the method comprising delivering first, second and third fluids to each of the plurality of lumens.

The same or different first, second and third fluids may be delivered to each of the plurality of lumens. Optionally, at least one of the first, second and third fluids have a different flow rate than another of the fluids within the lumen. Also, at least one of the first, second and third fluids may have the same flow rate than another of the fluids within the lumen.

Also according to this embodiment, the first, second and third fluids may be combined to form different crystallization conditions for crystallizing a molecule such as a protein. In one variation, the first, second and third fluids combine to form different crystallization conditions, the second fluid comprising the material to be crystallized and being positioned between the first and third fluids.

In regard to the various embodiments where a device is rotated about one or more rotational axes, the device may optionally be designed so that any or more of the following conditions are satisfied: the first and second rotational axes are laterally offset relative to each other; the first and second rotational axes are at an angle relative to each other and intersect; the first and second rotational axes are at an angle relative to each other and are laterally offset; the first and second rotational axes are perpendicular to each other and intersect; the first and second rotational axes are perpendicular to each other and are laterally offset; the first and second rotational axes are at an angle of 45 degrees relative to each other and intersect; the first and second rotational axes are at an angle of 45 degrees relative to each other and are laterally offset; and the first and second rotational axes are parallel and laterally offset relative to each other.

According to any of the embodiments employing centrifugal forces, the devices may be designed so that material is optionally moved within at least 4, 8, 12, 24, 96, 200, 1000 or more different microvolumes in a same manner when the centrifugal forces are applied.

Also according to any of the embodiments employing centrifugal forces, the devices may be designed so that the volume of fluid or other material delivered to a submicrovolume in a given microvolume is within 50%, 25%, 10%, 5%, 2%, 1% or less of the volume of fluid or other material delivered to a corresponding submicrovolume in any other microvolume.

Optionally, the centrifugal forces are applied such that a same centrifugal force is applied to material in each of the plurality of microvolumes.

Optionally, the centrifugal forces are applied such that at least 0.01 g, 0.1, 1 g, 10 g, 100 g or more force is applied to the material in the device to cause the material to move within the microvolumes.

Applying the centrifugal forces may be performed by rotating the device. Optionally, the centrifugal forces are applied by rotating the device at least 10 rpm, 50 rpm, 100 rpm or more.

In regard to all of the above embodiments, unless otherwise specified, microvolumes may have a variety of shapes including, but not limited to lumens and microchambers, When a lumen is employed, the lumen optionally has a cross sectional diameter of less than 2.5 mm, optionally less than 1 mm, and optionally less than 500 microns.

A variety of different substrates may be used to make the microfluidic devices of the present invention. In one variation, the substrate comprises one or more members of the group consisting of polymethylmethacrylate, polycarbonate, polyethylene terepthalate, polystyrene, styrene copolymers, glass, and fused silica. In one variation, the substrate is optically transparent.

According to each of the above embodiments, the experiment being performed may optionally be a crystallization of a molecule or material. The crystallization may optionally be of a biomolecule. Examples of biomolecules that may be crystallized include, but are not limited to viruses, proteins, peptides, nucleosides, nucleotides, ribonucleic acids, and deoxyribonucleic acids.

It is also noted that the material to be crystallized may contain one, two or more materials selected from the group consisting of viruses, proteins, peptides, nucleosides, nucleotides, ribonucleic acids, deoxyribonucleic acids, small molecules, drugs, putative drugs, inorganic compounds, metal salts, organometallic compounds and elements. In one variation, the material to be crystallized is a macromolecule with a molecular weight of at least 500 Daltons.

In certain embodiments, a spectroscopic analysis is performed. The spectroscopic analysis may optionally be selected from the group consisting of Raman, UV/VIS, IR, x-ray spectroscopy, polarization, and fluorescent. In one particular variation, the spectroscopic analysis is x-ray spectroscopy In a further particular variation, the x-ray spectroscopy is x-ray diffraction.

In some instances, the spectroscopic analysis involves an x-ray traversing the microfluidic device. In such instances, a groove may be employed in the device that is sufficiently deep relative to the second face of the substrate within the overlapping lateral footprint that when the portion of the microvolume within the overlapping lateral footprint comprises a crystallization sample and an x-ray beam traverses the card shaped substrate at the overlapping lateral footprint, the portion of the microvolume that the x-ray beam traverses contains at least half as many electrons as is contained in the substrate where the x-ray beam traverses. Optionally, the portion of the microvolume that the x-ray beam traverses contains at least as many electrons as is contained in the substrate where the x-ray beam traverses. Preferably, the portion of the microvolume that the x-ray beam traverses contains at least three, five, ten times or more times as many electrons as is contained in the substrate where the x-ray beam traverses.

Each of the above embodiments may optionally include transporting material within the microfluid device. Such transport may be performed by a variety of different methods. For example, transporting may be performed by a method selected from the group consisting of electrophoresis, electroosmotic flow and physical pumping. In one variation, transporting is performed by electrokinetic material transport. In some instances, transporting is performed by moving the device. This may be done by applying a centrifugal force, which in turn may be performed by rotating the device about a rotational axis.

Each of the above embodiments may optionally include the use of one or more dividers to separate aliquots of materials. In some instances, the separated aliquots of materials correspond to separate experiments such as crystallization trials. The dividers may be formed of a variety of different materials. For example, the dividers may be formed of a permeable, semi-permeable or impermeable material that may be a gas, liquid, gel, or solid. In one particular variation, the one or more dividers are selected from the group consisting of a membrane, gel, frit, and matrix.

The one or more dividers may form various interfaces including those selected from the group consisting of liquid/liquid, liquid/gas interface, liquid/solid and liquid/sol-gel interface.

The one or more dividers optionally function to modulate diffusion characteristics between adjacent crystallization samples. For example, the one or more dividers may be formed of a semi-permeable material that allows diffusion between adjacent crystallization samples.

These and other methods, devices, compositions and kits are described herein.

BRIEF DESCRIPTION OF THE DRAWINGS

FIG. 3A illustrates various interconnections that may be formed between different lumens.

FIG. 3B illustrates how two sub-lumens extending from and joining with a main lumen may be used to effect mixing within the main lumen.

FIG. 3C illustrates the use of a dividing feature to separate a crystal containing crystallization experiment into two portions.

FIG. 3D illustrates different combinations of single and double ports that may be combined for complex mixing, separation, diffusion and purifications.

FIG. 4A illustrates a crystallization mixture performed within a lumen positioned between two dividers, FIG. 4B illustrates a crystallization performed within a lumen where multiple crystallization conditions are simultaneously employed.

FIG. 4C illustrates a crystallization performed within a lumen where a series of crystallization agents are set up for crystallization against a series of substances to be crystallized.

FIG. 5A illustrates a crystallization performed within a lumen where one or more of the elements of the crystallization experiment change along a length of the lumen. The change can occur discretely or continuously, and need not be changed in a simple linear method.

FIG. 5B illustrates a crystallization performed within a lumen where a series of substances to be crystallized are in a single gradient.

FIG. 5C illustrates a crystallization performed within a lumen where a series of crystallization agents can be assayed against a substance to be crystallized.

FIG. 5D illustrates diffusion between various elements in a crystallization performed within a lumen.

FIG. 6A illustrates a crystallization performed within a lumen where a single crystallization condition occupies an entire crystallization space.

FIG. 6B illustrates multiple crystallizations being performed within a lumen where dividers are used between the crystallizations, the dividers being shown to have planar surfaces adjacent the crystallizations.

FIG. 6C illustrates multiple crystallizations being performed within a lumen where dividers are used between the crystallizations, the dividers being shown to have curved, convex surfaces adjacent the crystallizations.

FIG. 7A shows a device for performing a series of crystallizations within a series of lumens where each lumen comprises a loading and unloading port and a lumen body interconnecting the ports.

FIG. 7B shows a cross section of a device for performing a crystallization within a lumen where the lumen is not enclosed.

FIG. 7C shows a cross section of a device for performing a crystallization within a lumen where the lumens are rectangular in shape.

FIG. 7D shows a cross section of a device for performing a crystallization within a lumen where the lumens are curved or tubular in shape.

FIG. 7E shows a device for performing crystallizations within a series of lumens where the lumens are loaded with samples that are separated by divider or modifier segments. It should be appreciated that each discrete sample may have conditions that are potentially unique and unrelated to adjacent samples. The dividers or modifiers positioned between the samples can be permeable, semi-permeable or impermeable.

FIG. 8A shows a device for performing a series of different crystallizations within a series of lumens where each lumen comprises a loading and unloading port and a lumen body interconnecting the ports.

FIG. 8B illustrates a single lumen in which a barrier is adjacent to the crystallization condition bounded by second barrier.

FIG. 8C illustrates a lumen comprising a more complex design of crystallizations than the lumen shown in FIG. 8B.

FIG. 8D illustrates a multi-component crystallization being performed in a single lumen.

FIG. 9B illustrates an enlargement of a lumen of the device shown in FIG. 9A which illustrates some of the different simultaneous diffusions that are made possible by the invention.

FIG. 10A illustrates an embodiment of a device comprising first and second lumens where the first and second lumens share a common wall that allows for diffusion between the lumens over at least a portion of the length of the lumens.

FIG. 10B illustrates an embodiment of a device comprising first, second and third lumens where the first, second and third lumens share a common wall that allows for diffusion between the lumens over at least a portion of the length of the lumens.

FIG. 10C illustrates a crystallization experiment loaded into a double lumen device such as the device shown in FIG. 10A.

FIG. 10D illustrates diffusion having occurred both through the semi-permeable internal divider, as well as through the permeable or semi-permeable wall of the device shown in FIG. 10C.

FIG. 10E illustrates the experiment shown in FIG. 10D where a series of crystal growths have occurred after some diffusion has occurred.

FIG. 10F illustrates a device with multiple lumens that may each be separated by permeable or semi-permeable wall.

FIG. 12A illustrates a device comprising a series of lumens, each lumen having attached to it an array of individual crystallization cells, each cell having at least one separate inlet or outlet and at least one channel connecting the cell to the lumen.

FIG. 12B illustrates an embodiment of an individual crystallization cell shown in FIG. 12A.

FIG. 12C illustrates an embodiment of an individual crystallization cell shown in FIG. 12A where the cell comprises a crystallization agent and a substance to be crystallized.

FIGS. 15A–15G illustrate an embodiment of a centrifugally driven crystallization device.

FIG. 15A illustrates a repeating unit of the centrifugal array.

FIG. 15B illustrates a process for using a centrifugal device.

FIG. 15C illustrates the effect of centrifugal force on the samples that are loaded in the centrifugal device illustrated in FIG. 15B.

FIG. 15D illustrates what happens when the centrifugal force vector is changed such that the force now directs the excess crystallization agent and excess material to be crystallized toward the waste ports via the respective waste channels.

FIG. 15E illustrates each channel of the centrifugal device filled to point V, resulting in precise volume measurements.

FIG. 15F illustrates what happens when the centrifugal force vector has been altered to align in the direction shown.

FIG. 15G illustrates crystallization chamber filled with the combination of the material to be crystallized and the crystallization agent, or agents.

DETAILED DESCRIPTION OF THE INVENTION

Figure 1A:
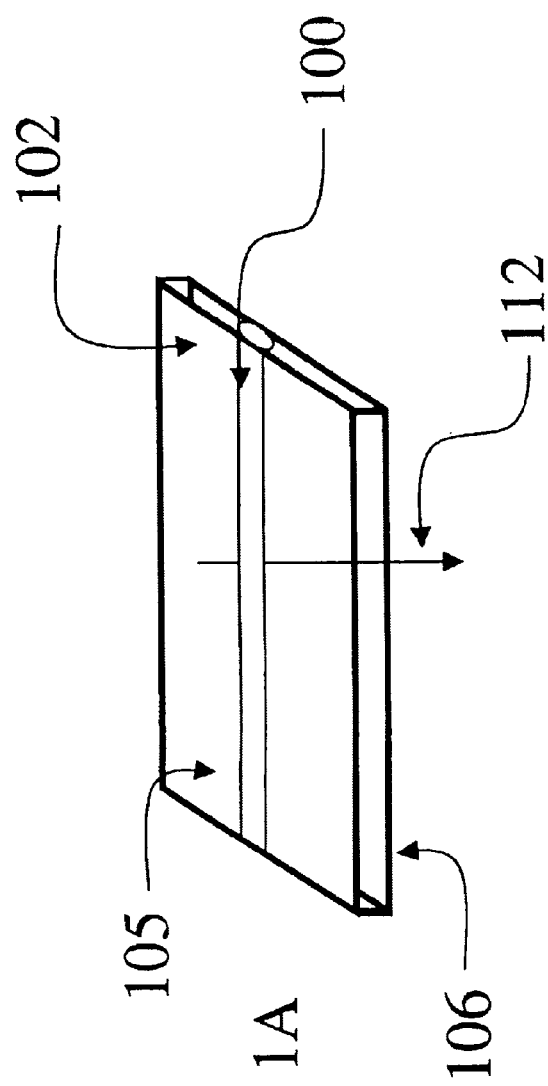
FIG. 1A illustrates a card shaped device housing microvolumes with opposing faces.

The present invention relates to various methods, devices and kits relating to microfluidics.

One particular aspect of the present invention relates to the use of these methods and devices for forming crystallization samples, transporting crystallization samples, and crystallizing materials therein, particularly on a microvolume scale, high throughput manner, Distinguishing the present invention in this regard is the performance of the crystallizations in very small, substantially enclosed volumes formed by or within a substrate, referred to herein as an "enclosed microvolume". Other aspects of the present invention will be understood by one of ordinary skill in view of the teachings provided herein.

It is noted that many of the particular embodiments are described herein in regard to performing crystallization experiments. However, it should be understood that many of the operations involved in performing crystallization experiments (e.g., measuring, mixing, fluid flow and analysis) made possible by the various devices and methods of the present invention have applications outside of performing crystallization experiments and should therefore not be limited to crystallization experiments, A "crystallization sample", as the term is used herein, refers to a mixture comprising a material to be crystallized. The crystallization includes such other components in the mixture to cause or at least attempt to cause crystals of the material to be formed in the mixture.

According to the present invention, crystallization samples are formed, transported, and crystallization attempts conducted in enclosed microvolumes. These enclosed microvolumes comprise one or more lumens and optionally microchambers in fluid communication with the lumens. The lumens are enclosed within a substrate. When employed, microchambers are enclosed microvolumes defined within the substrate in fluid communication with the lumens. The lumens and microchambers provide an encased environment within which crystallization samples may be formed, and crystallization attempts performed and analyzed.

The term "lumen" as the term is used herein, refers to any elongated, enclosed volume formed at least partially by a substrate. The lumen preferably has a cross sectional diameter of less than 2.5 mm, preferably less than 1 mm and more preferably less than 500 microns. In one variation, the lumen has a cross sectional diameter between 0.1 microns and 2.5 mm, preferably between 0.1 microns and 1 mm, and preferably between 0.1 and 500 microns. Aside from openings in the lumen, most typically adjacent the proximal and distal ends of the lumen, the lumen provides an enclosed environment in which to form, transport, conduct, and optionally analyze crystallizations.

Mass flow may be reduced by controlling the length of the crystallization volume within the microlumens. This serves to reduce the forces driving convection currents within the crystallization condition. By minimizing the length of the crystallization volume within the microlumens, facile control of the degree of convection currents within the microlumen is controlled.

In certain instances, it may be desirable for the lumen to be in fluid communication with one or more microchambers. A "microchamber", as the term is used herein, refers to a volume in fluid communication with a lumen that has a larger cross sectional area than the lumen.

By forming crystallization conditions and performing crystallizations within the small, relatively sealed volumes defined by the enclosed microvolumes of the lumens and microchambers, a variety of different advantages are provided.

One advantage provided by conducting crystallizations in enclosed microvolumes is that it facilitates parallel screening of many materials at once or a material in many conditions at once, or a combination thereof.

A further advantage provided by the small volumes associated with performing crystallizations in enclosed microvolumes is that it enables the conservation of the material to be crystallized, thereby enabling greater numbers of crystallization conditions to be sampled using a given amount of material. By achieving higher densities of crystallization conditions, advancements in crystal analysis are obtained.

A further advantage provided by performing crystallizations according to the present invention is a reduction in evaporation during the preparation and performance of the crystallization. As a result, crystallization conditions can be more precisely controlled and remain stable for longer periods of time. Crystallizations can also be conducted over a wider range of temperature conditions since losses due to evaporation are significantly curtailed.

A further advantage provided by performing crystallizations according to the present invention is a further reduction in the space requirements for performing crystallizations. More specifically, the present invention allows multiple crystallizations to be performed in a denser format. This allows the device within which the crystallizations are performed to be smaller and allows more crystallizations to be performed in a single device. For example, when in situ crystallizations are performed in a thin cassette or card, the crystallizations may be densely packed, allowing for rapid and efficient analysis of the crystallization conditions.

A further advantage provided by performing crystallizations according to the present invention is the more rapid equilibration times that may be achieved by further reducing crystallization volumes.

A further advantage provided by performing crystallizations according to the present invention is the number of parallel experiments that may be performed. For example, embodiments of the present invention provide for the use of at least 4, 8, 12, 24, 96, 200, 1000 or more different microvolumes in parallel. In regard to the use of centrifugal forces, the devices may be designed so that material is moved within at least 4, 8, 12, 24, 96, 200, 1000 or more different microvolumes in a same manner when the centrifugal forces are applied.

Yet a further advantage provided by performing crystallizations according to the present invention is the precision with which fluid and material can be transported. For example, certain embodiments use centrifugal forces to transport materials. By being able to closely control the sizes of the microvolumes, devices can be designed so that the volume of fluid delivered to a given submicrovolume of a given microvolume upon rotation of the device is within 50%, 25%, 10%, 5%, 2%, 1% or less of the volume of fluid delivered to submicrovolumes of other microvolumes.

As will be evident from the foregoing description of the operation of the devices of the present invention, a further advantage provided is simplified material handling.

1. Materials To Be Crystallized

While problems associated with crystal growth addressed by the present invention are of particular interest for proteins and other biomolecules, it is a general problem of all crystal forming materials. The materials to be crystallized may be any substance capable of crystallizing or co-crystallizing. For example, the material to be crystallized may contain one, two or more materials selected from the group consisting of viruses, proteins, peptides, nucleosides, nucleotides, ribonucleic acids, deoxyribonucleic acids, ligands, small molecules, drugs, putative drugs, inorganic compounds, metal salts, organometallic compounds and elements and mixtures and combinations thereof.

The materials to be crystallized may be any material for which a crystal structure is needed. Determining high-resolution structures of materials by a high-throughput method such as the one of the present invention can be used to accelerate the analysis of materials, especially drug development.

The material to be crystallized may also be a molecule for which a crystalline form of the molecule is needed. For example, it may be desirable to create a crystalline form of a molecule or to identify new crystalline forms of a molecule. In some instances, particular crystalline forms of a molecule may have greater biological activity, dissolve faster, decompose less readily, and/or be easier to purify.

The material to be crystallized may also be a combination of substances for the production of co-crystals. The co-crystals can comprise any two of a small molecule, a drug, a ligand, a substrate, an inhibitor, a guest chemical, protein, nucleotide, or a protomer. The substances can be a plurality of small molecules, drugs, ligands, substrates, inhibitors, guest chemicals, proteins, or a protomers.

The material to be crystallized is preferably a macromolecule such as a protein but may also be other types of macromolecules. The molecule preferably has a molecular weight of at least 500 Daltons, more preferably at least 1000 Daltons, although smaller molecular weight molecules may also be crystallized.

2. Construction of Enclosed Microvolumes

The construction, design and operation of various different microfluidic devices have been described in literature and are thus known in the art. For example, U.S. Pat. Nos. 5,126,022; 5,296,114; 5,180,480; 5,132,012; and 4,908,112 are examples of references detailing the design and construction of lumens and microchambers in a substrate. Other examples of references include Harrison et al., "Micromachining a Miniaturized Capillary Electrophoresis-Based Chemical Analysis System on a Chip," Science (1992) 261: 895; Jacobsen et al., "Precolumn Reactions with Electrophoretic Analysis Integrated on a Microchip," Anal. Chem. (1994) 66: 2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348. Further examples of different microfluidic devices include, but are not limited to those described in: U.S. Pat. Nos. 6,306,273, 6,284,113, 6,176,962, 6,103,537, 6,093,296, 6,074,827, 6,007,690, 5,858,188, 5,126,022, 5,750,015, 5,935,401, 5,770,029 assigned to Aclara, Inc.; U.S. Pat. Nos. 6,321,791, 6,316,781, 6,316, 201, 6,306,272, 6,274,337, 6,274,089, 6,267,858, 6,251,343, 6,238,538, 6,235,175, 6,221,226, and 6,186,660 assigned to Caliper, Inc.; PCT Application Nos. WO 01/94635, WO 01/75176, WO 01/67369, WO 01/32930, WO 01/01025, WO 99/61888, each assigned to Fluidigm, Inc.; U.S. Pat. Nos. 6,319,472, 6,238,624 assigned to Nanogen, Inc.; U.S. Pat. Nos. 6,290,685 assigned to 3M Corp.; as well as U.S. Pat. Nos. 6,261,430, 6,251,247, 6,236,945, 6,210,986, 6,176,990, 6,007,690, 6,074,827, 6,056,860, 6,054,034, 5,885,470, 5,858,195, 5,750,015, 5,571,410, 5,580,523, 5,296,114, 5,180,480, 5,132,012, 5,126,022, 4,891,120, and 4,908,112.

It should be understood that these numerous examples are only intended to be illustrative in regard how enclosed microvolumes according to the present invention may be constructed, designed and operated in conjunction with the present invention.

Transport of material within the microfluidic devices of the present invention may be performed by any mode of transport available to microfluidic devices including, but not limited to electrophoresis, electroosmotic flow and physical pumping. In one variation, transporting is performed by electrokinetic material transport. A novel feature of certain embodiments of the present invention, discussed herein in greater detail, is the use of centrifugal force to transport material, for example by rotating the device about a rotational axis.

The enclosed microvolumes may be formed in any substrate within which microvolumes may be formed. Examples of suitable substrates include, but are not limited to glass, fused silica, acrylics, thermoplastics, and the like. The various components of the integrated device may be fabricated from the same or different materials, depending on the particular use of the device, the economic concerns, solvent compatibility, optical clarity, color, mechanical strength, and the like.

For applications where it is desired to have a disposable device, due to ease of manufacture and cost of materials, the device will typically be fabricated from a plastic. For ease of detection and fabrication, the entire device may be fabricated from a plastic material that is optically transparent, as that term is defined above, Particular plastics finding use include polymethylmethacrylate, polycarbonate, polyethylene terepthalate, polystyrene or styrene copolymers, and the like. It is noted that these various materials may be used alone or in combination to form the devices of the present invention.

The substrate comprising the enclosed microvolumes may be in any form, e.g., a tube, a card, a chip or a block. The substrate is preferably in the form of a card. The card preferably has a face sized less than 12 cm×8.5 cm. The enclosed microvolumes may be formed by any process by which an enclosed lumen or chamber may be created in a material. For example, the shape of the substrate and the enclosed microvolumes may be formed by thermoplastic injection molding, micromolding, punching, milling, any solid free form technology, such as three dimensional printing, or other types of manufacturing technologies for plastics, such as micromolding, embossing, laser drilling, extrusion, injection, or electron deposition machining, glass or silicon, conventional silicon processing technology, such as photolithography, deep reactive ion or wet etching, electron beam machining, micromachining, electro-discharge machining, reaction injection molding.

It is noted that the substrate comprising the enclosed microvolume may be formed of a single material, such as a block or a card. Alternatively, one or more materials may be brought together to form the enclosed microvolume. This typically involves having a portion of the microvolume be formed by a first substrate (e.g., photolithography on a surface of the first substrate). A second substrate is brought together with the first substrate to complete the definition of the enclosed microvolume. The act of combining the first and second substrates can cause the material to be crystallized to be enclosed. The act of combining can also cause mixing to occur.

The substrate is preferably optically clear, transparent, translucent or opaque. The substrate is preferably formed of a material that allows for various spectroscopic analyses (e.g., Raman, UVNVIS, IR or x-ray spectroscopy, polarization, fluorescent, and with suitable designs, x-ray diffraction) to be performed in situ. In one particular variation, the spectroscopic analysis is x-ray spectroscopy. In a further particular variation, the x-ray spectroscopy is x-ray diffraction.

In order to improve the performance of the device for performing in situ x-ray spectroscopy such as x-ray diffraction and other forms of spectroscopy where an x-ray is caused to traverse the substrate, the number of electrons in the path of the x-ray beam of the material being analyzed should be maximized relative to the number of electrons that is otherwise in the path of the x-ray beam.

The number of electrons of the device that are traversed can be reduced by choosing materials to form the device that have a low atomic number (Z), or a low density. Examples of materials that are preferably used for reducing the number of electrons in the substrate material include low density plastics such as polystyrene, polyethylene, polypropylene and other carbon based polymers. Silicon materials, such as silicon wafers, glass, including borosilicate and soda glass, and aerogels can be suitable materials. Optically opaque materials that are suitable include Beryllium, plastic films and plastics.

A key parameter R, corresponds to a ratio between the number of electrons within the sample, (e.g., the precipitate, oil, crystal and optionally other contents of the microvolume) that the x-ray traverses, and the sum of the electrons contained in the support material and the lid, or sealing material that the x-ray traverses.

$$R = \frac{\sum [e^-]_{Crystal}}{\sum [e^-]_{Cassette}},$$

where the number of electrons in the x-ray beam, $[e^-]$, is calculated by multiplying the density of the material in grams, , by thickness of the material and the area of the x-ray beam at the microlumen, which gives the mass in grams, X, of the microlumen material in the x-ray beam. This can be converted into the number of electrons by multiplying the mass in grams by Avogadro's number, N, and dividing by the molecular weight of the material, MW. i.e., $[e^-]=X*N/MW$.

The contents of the microvolume that the x-ray beam traverses preferably contains at least half as many electrons as is contained in the substrate where the x-ray beam traverses. More preferably, the portion of the microvolume that the x-ray beam traverses contains at least one, three, five, ten times or more as many electrons as is contained in the substrate where the x-ray beam traverses.

In some instances, it is a particular precipitate, oil, or crystal that is being analyzed. It is also preferred that the particular precipitate, oil, or crystal that the x-ray beam traverses contains at least half as many electrons as is contained in the device where the x-ray beam traverses More preferably, the particular precipitate, oil, or crystal that the x-ray beam traverses should contain at least one, three, five ten times or more as many electrons as is contained in the device where the x-ray beam traverses.

The number of electrons in the path of the incident x-rays can be reduced by minimizing the mass of material in the path. Accordingly, the substrate enclosing the microvolumes preferably contains as little material as possible in the direction of the path of the x-rays. As illustrated in FIG. 1A, the device housing the microvolumes 100 will most commonly have a card shape 102 with opposing faces 104 and 106. Walls 108, 110 (shown in FIGS. 1B and 1C) adjacent the opposing faces define a portion of the microvolume. X-rays 112 will typically traverse the card substantially perpendicular to the opposing faces in order to minimize the path length across the card, that path length being defined largely by the thickness of walls 108, 110. It is desirable for the card to have sufficient thickness so that it will be sufficiently rigid for necessary handling. However, by reducing the amount of material forming the walls 108, 110 adjacent a portion of the microvolume where x-rays will be incident, one can reduce the amount of mass in the path of the x-rays.

Figure 1B:
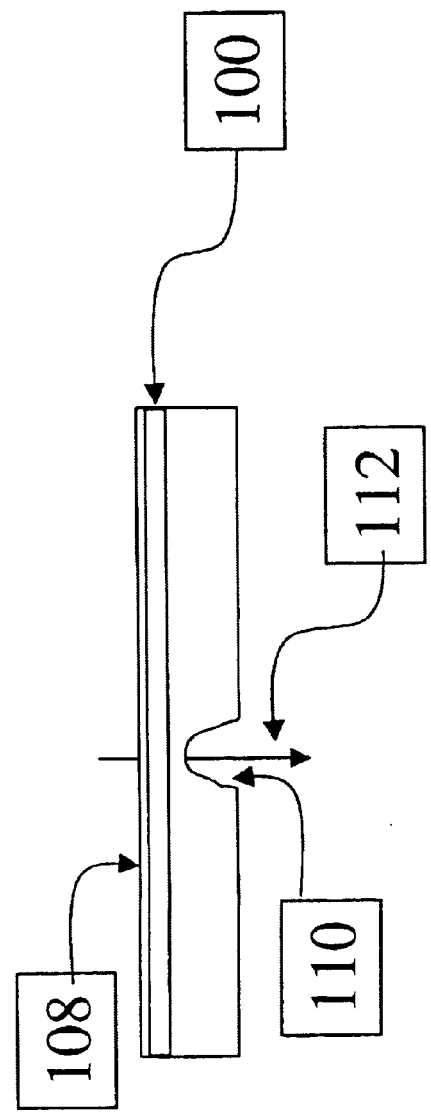
FIG. 1B illustrates an embodiment of a card shaped device where the thickness of the overall card is reduced adjacent a region where x-rays will be incident in order to reduce the amount of material in the path of the x-rays.

FIG. 1B illustrates an embodiment where the thickness of the overall card is reduced adjacent a region where x-rays will be incident in order to reduce the amount of material in the path of the x-rays.

Figure 1C:
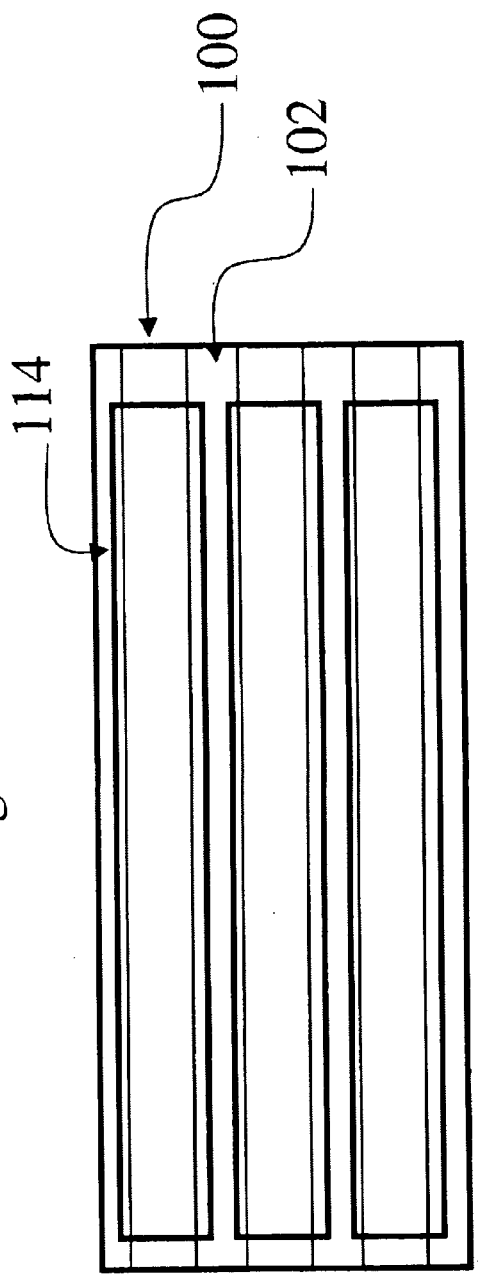
FIG. 1C illustrates a bottom up view of an embodiment of a card shaped device where grooves have been created so that less material is present adjacent a region where x-rays will be incident.
Figure 1D:
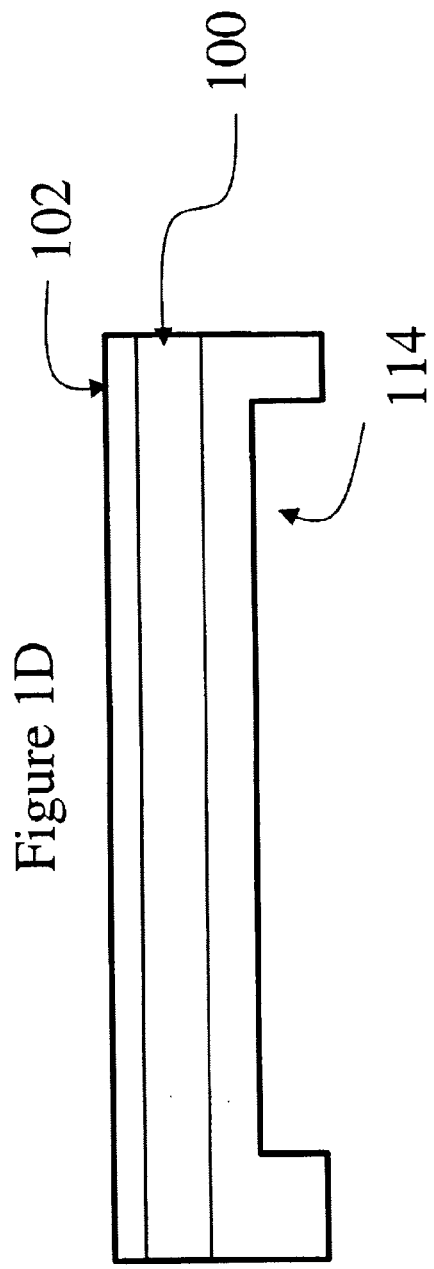
FIG. 1D illustrates a cross sectional view of an embodiment of a card shaped device where grooves have been created so that less material is present adjacent a region where x-rays will be incident.

FIGS. 1C and 1D illustrate an embodiment where less material is present adjacent a region where x-rays will be incident in order to reduce the amount of material in the path of the x-rays. This may be accomplished by forming a card as shown in FIG. 1C with grooves 114 on one or both sides adjacent where x-rays will be incident. As used herein, a groove refers to any recess formed in the substrate so that the thickness of the device is reduced.

If the microvolume is closely adjacent one face of the card, a groove may be formed adjacent the opposite side of the card as shown in the cross sectional view provided by FIG. 1D. It is noted that the card may be formed with the groove or may be formed without the groove and then material may be removed from the card to create the groove.

At least a portion of a groove is preferably positioned within a lateral footprint of the microvolume where it is desired to have the x-ray beam traverse the device. Accordingly, one embodiment of the invention relates to a microfluidic device that comprises: a card shaped substrate having first and second opposing faces; one or more microvolumes at least partially defined by a first face of the card shaped substrate; and one or more grooves at least partially defined by a second face of the card shaped substrate; wherein a lateral footprint of at least a portion of the one or more grooves overlaps with a lateral footprint of at least one of the one or more microvolumes.

At the overlap, the groove is preferably sufficiently deep that an x-ray beam traversing the device encounters at least half as many electrons within the microvolume as the remainder of the device that the x-ray beam traverses. More preferably, the x-ray beam traversing the device encounters at least one, three, five, ten times or more as many electrons within the microvolume as the remainder of the device that the x-ray beam traverses.

As illustrated in FIG. 1C, the microvolume may be a lumen. The groove may have a longitudinal axis that is aligned with a longitudinal axis of the lumen adjacent the overlapping lateral footprint (shown in FIG. 1C). This provides a greater area for the x-ray beam to traverse within the overlap. It is recognized, however, that the groove may not have a longitudinal axis or may have a longitudinal axis that is misaligned, optionally to the extent of being perpendicular to a longitudinal axis of the lumen adjacent the overlapping lateral footprint.

By reducing the amount of substrate encountered by an x-ray beam, for example by using devices with grooves such as those shown in FIGS. 1C and 1D, methods may be performed according to the present invention comprising: performing an experiment in a microvolume of a microfluidic device; and performing a spectroscopic analysis using an x-ray beam that traverses the microfluidic device such that material within the microfluidic device that the x-ray beam traverses contains at least as many electrons as is otherwise traversed when the x-ray beam traverses the microfluidic device. Optionally, the material within the microfluidic device that the x-ray beam traverses contains at least three, five, ten times or more as many electrons as is otherwise traversed when the x-ray beam traverses the microfluidic device.

As will be illustrated herein, crystallization conditions may be formed by delivering different components to a single lumen or by delivering different components to a given lumen or microchamber from multiple different lumens In this regard, the multiple different lumens are preferably interconnected.

The cross sectional shape of the lumen may stay the same or may vary along the length of the lumen. Optionally, the lumen may be connected to one or more chambers to which material from the lumen is delivered or from which material is delivered to the lumen. It is noted that crystallizations may also be performed in the chambers after material is delivered via the lumen to the chamber.

The lumen may have a variety of cross sectional geometries. For example, the cross-sectional geometry of the lumen may be circular, semi-circular, ovoid, "U" shaped, square, or rectangular, or one or more combinations thereof. Preferably, the cross sectional area of the lumen is small relative to the length of the lumen. This serves to reduce convection currents within liquids passing within the lumen. Convection currents may be further reduced by the use of thixotropic agents, such as silica gel, agarose, other polysaccharides and polymers.

3. Layout and Use of Microsized Lumens For Performing Crystallization Trials Various methods and devices are provided for performing crystallization trials in microfluidic devices. For example, in one embodiment, a method is provided for determining crystallization conditions for a material, the method comprising: taking a plurality of different crystallization samples in an enclosed microvolume, the plurality of crystallization samples comprising a material to be crystallized and crystallization conditions that vary among the plurality of crystallization samples; allowing crystals of the material to form in the plurality of crystallization samples; and identifying which of the plurality of crystallization samples comprise a precipitate, oil or a crystal of the material.

In another embodiment, a method is provided for determining crystallization conditions for a material, the method comprising: taking a plurality of different crystallization samples in a plurality of enclosed microvolumes, each microvolume comprising one or more crystallization samples, the crystallization samples comprising a material to be crystallized and crystallization conditions which vary among the plurality of crystallization samples; allowing crystals of the material to form in plurality of crystallization samples; and identifying which of the plurality of crystallization samples comprise a precipitate, oil or a crystal of the material.

In another embodiment, a method is provided for determining crystallization conditions for a material, the method comprising: taking a microfluidic device comprising one or more lumens having microvolume dimensions and a plurality of different crystallization samples within the one or more lumens, the plurality of crystallization samples comprising a material to be crystallized and crystallization conditions that vary among the plurality of crystallization samples; transporting the plurality of different crystallization samples within the lumens; and identifying a precipitate or crystal formed in the one or more lumens. Transporting the plurality of different crystallization samples within the one or more lumens may be performed by a variety of different methods. For example, transporting may be performed by a method selected from the group consisting of electrophoresis, electroosmotic flow and physical pumping. In one variation, transporting is performed by electrokinetic material transport. In a variation according to this embodiment, at least one of the lumens optionally comprises a plurality of different crystallization samples.

In another embodiment, a method is provided for determining crystallization conditions for a material, the method comprising: taking a microfluidic device comprising one or more lumens having microvolume dimensions and a plurality of different crystallization samples within the one or more lumens, the plurality of crystallization samples comprising a material to be crystallized and crystallization conditions that vary among the plurality of crystallization samples; transporting the plurality of different crystallization samples within the one or more lumens; and identifying a precipitate or crystal formed in the one or more lumens; and performing a spectroscopic analysis on the identified precipitate or crystal while within the lumen.

The method may optionally further include forming the plurality of different crystallization samples within the one or more lumens. The plurality of crystallization samples may be comprised in a single lumen or multiple lumens.

According to any of these embodiments, the methods may further comprise forming the plurality of different crystallization samples within the one or more lumens. The plurality of crystallization samples may be comprised in a single lumen or a plurality of lumens.

Also according to any of these embodiments, one or more dividers may optionally be positioned between different crystallization samples in the enclosed microvolumes to separate adjacent crystallization samples.

Figure 2:
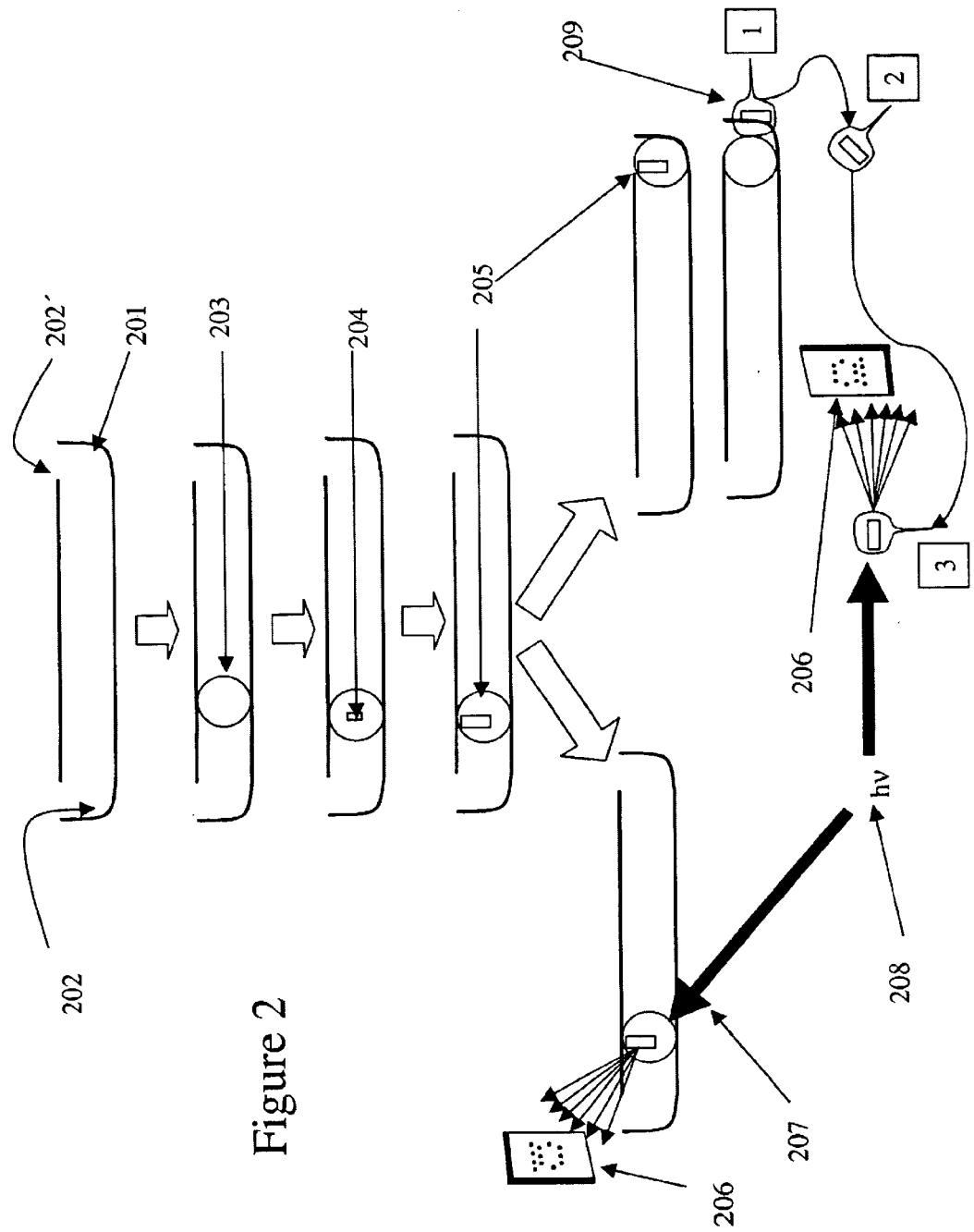
FIG. 2 illustrates the generalized use of a microvolume dimensioned lumen to form crystallization samples and perform crystallization.

A generalized use of a microfluidic sized lumen to form crystallization samples and perform crystallization attempts is illustrated in regard to FIG. 2. As shown in step A of FIG. 2, an enclosed lumen 201 is provided such that the lumen 201 has at least one opening 202A adjacent a first end of the lumen and at least one opening 202B adjacent a second end of the lumen. A crystallization experiment 203 is introduced into the lumen 201 via one of the openings, as shown in step B. This material may be a pre-formed crystallization experiment, consisting of a material to be crystallized and one or more crystallization agents, or it may be a material to be crystallized that will undergo a diffusion experiment, wherein material will be transferred either through vapor or liquid diffusion. Step C of the figure shows the crystallization experiment proceeding such that a portion of the material either crystallizes into a crystal 204 or a plurality of crystals, microcrystals, needles, precipitates or other solids, or the material remains in solution.

If a crystal forms, as shown in step D of the figure (shown as 205), then the crystal, precipitate, oil, etc. may be examined in situ, for example, as shown in steps E–H. Examination may be performed by any available method, including, but not limited to spectroscopically, visually, or if the crystallization channel is suitably designed, by direct exposure of x-rays. As shown by the arrows leading from step D, the crystal or crystallization mixture may be harvested from the lumen.

Steps E–H show different processing steps that may be performed on the crystal or crystallization mixture. Step E illustrates a crystal being examined within a lumen via x-ray diffraction by using an x-ray source 208 suitable for diffraction experiments, which is suitably focused and collimated to pass through the material to be examined. The diffracted x-rays can then be examined through the use of a suitable x-ray detector 206, which can be x-ray film, one dimensional x-ray detectors, two dimensional (area) detectors, or an electronic x-ray detector or scintillator. Alternatively, as shown in step F, the crystal 205 can be manipulated within the crystallization channel. This enables the harvesting of the crystal as shown in step G, wherein the crystal containing crystal experiment is brought to an outlet of the crystal channel.

As shown, the crystal can be harvested into an intermediate device, or may be harvested directly with a mounting suitable for x-ray diffraction. This mounting can be a loop 209, as shown in step G, or it can be a capillary suitable for x-ray mounting, or a fiber, or a spatula. These techniques for harvesting and manipulating crystals are widely known. Once the crystal is harvested, the crystal can then be transported to an x-ray diffraction experiment shown as step H where the crystal can be mounted in a position to facilitate the diffraction experiment. It should be appreciated that the material to be analyzed may not be a single crystal. For example, the material may be twinned crystals, or a plurality of crystals grouped together, or a number of loose crystals, a precipitate, or an oil that can then be examined for crystalline elements.

The crystallization drop 203 can be created within the microlumen, or it can be mixed outside of the channel and introduced into the channel. The actual method for loading the channels will vary depending upon the necessities of the experiment. A crystallization mixture can be formed by the use of a syringe, such as a Hamilton syringe, or via a parallel robotic system such as the Tecam, wherein the relevant volume of material to be crystallized is drawn up into the syringe and then the relevant volume of the crystallization agent can be drawn up. The material may be dispensed directly into the loading port 202, or may be dispensed into or onto an intermediate surface or container for mixing. The material can be applied to the inlet port under pressure from the syringe, or may be loaded onto the upper surface of 201, such that the droplet covers the inlet port 202. The droplet can then be loaded into the microlumen by the application of a pressure difference to 202 and 202', either through pressure at 202 or through vacuum at 202'. Similarly, after the crystal has grown, the application of a pressure difference, either directly, or indirectly through a pressure transfer fluid, such as mineral oil or buffer, the crystal can be moved to the outlet port 202', for harvesting as shown above in steps 1–3 of FIGS. 2G and 2H.

It is noted that a given lumen may have multiple lumens interconnecting with it or extending from it. For example, as shown in FIG. 3A, a lumen 301 may have two inlet ports 302A and 302B and a junction 303 that may form an acute, perpendicular or obtuse intersection. A perpendicular intersection is illustrated in FIG. 3A where the intersection 304 of channels 302C and 302D is formed perpendicularly.

FIG. 3B illustrates how two sub-lumens extending from and joining with a main lumen may be used to effect mixing within the main lumen. Material 305A in one sub-lumen of the main lumen and material 305B in the second sub-lumen extending from the main lumen are joined and mixed together into a single volume 306 by the geometry of the interconnecting channels. Depending upon the particular application, the lumens and sub-lumens can be designed to affect differing levels of mixing and the alteration of the interface between the two substances. Obviously, the lumens may possess both combining features or dividing features or a combination thereof, or depending on the absolute and relative flows combining features that function as dividing features under altered fluid flows.

FIG. 3C illustrates the use of a dividing feature 303 to separate a crystal containing crystallization experiment 307 into two portions 308A and 308B. It should be understood that the relative volumes in 308A and 308B may be readily attained by, suitable design or practice, by achieving differential fluid flows.

It should also be appreciated that different combinations of single and double ports may be combined for complex mixing, separation, diffusion and purifications as illustrated in FIG. 3D. For example, as shown, ports 309A and 309B meet at junction 310A. Similarly, ports 309C, 309D meet at junction 310B. The sub-lumens from junctions 310B and 310C can intersect at 310A.

To generate the result shown in FIG. 3A, one might apply a sample to inlet port 302, block port 302', and apply a positive pressure difference between port 302 and the pressure within 301. This can be affected by applying a small vacuum at 301, by the removal of material from 301 hydraulically, or by the application of pressure at 302, or by the application of centrifugal force with a component along 301. The droplet can be brought to a stop at 303 by removing the motive force at such a time that the material comes to rest at 304. PID (Proportional-Integrating-differential) methods and/or controllers are very effective for optimizing fluid delivery accounting for hysteresis effects within the fluid transfer mechanisms and the microlumens.

In FIG. 3B, material can be applied at 302 and 302' and then individually advanced as described above, or may be advanced in tandem by the application of pressure differential across both fluids simultaneously to yield the combined mixture 306 at the union of the two microlumens.

FIG. 3C is constructed by inducing the material assembled in a crystallization bolus 306 to crystallize. Pressure can then be applied to the interior of the microlumen 301 to force the crystal containing bolus 307 along the microlumen 301 to the intersection 303. This pressure can be applied hydraulically to port 302 or 302', while sealing the other, or to both ports 302 and 302' simultaneously. The hydraulic pressure can be applied directly via syringe or syringe pump or via a hydraulic transfer fluid such as water or mineral oil using a fluid filled syringe or syringe pump, with or without a connecting manifold to facilitate the application of the hydraulic pressure to the ports 302 and 302'. At harvest, by modulating the pressure difference between two outlet ports, the unwanted crystallization liquor can be preferentially forced into the waste passage as bolus 308', while concentrating the crystal in a desired amount of crystallization liquor in bolus 308'. The pressure can be modulated by differential pumping of two syringe pumps connected to the respective outlet ports. This can be done under manual control with a simple joystick controller, or it can be accomplished with computer vision software, such as that provided by Keyance.

The methods and the devices of the present invention will now be described with regard to the following figures.

Figure 4A:
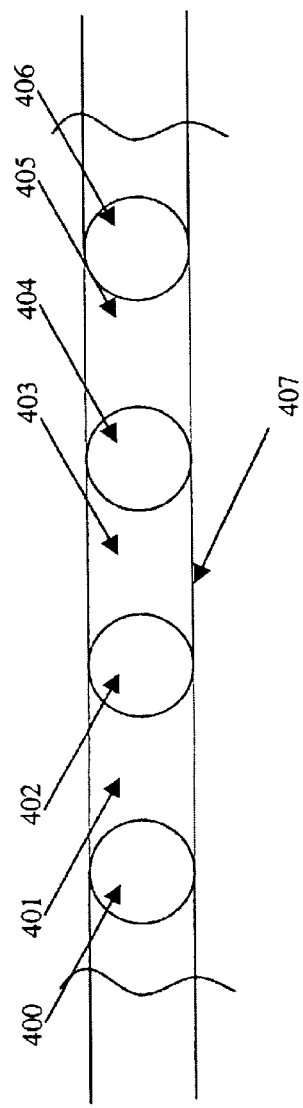
FIGS. 4A–4C provide several embodiments of performing crystallizations within a lumen.
Figure 4B:
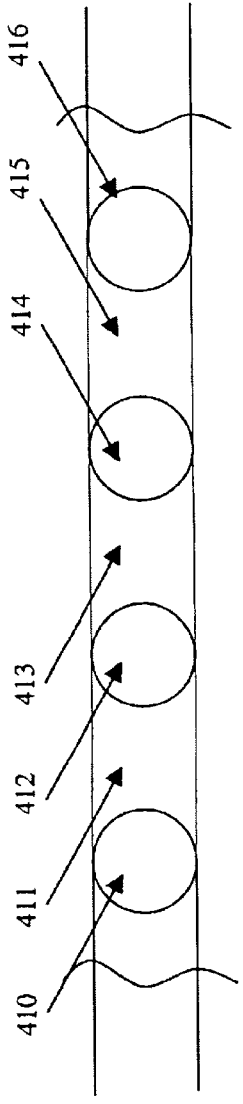
Figure 4C:
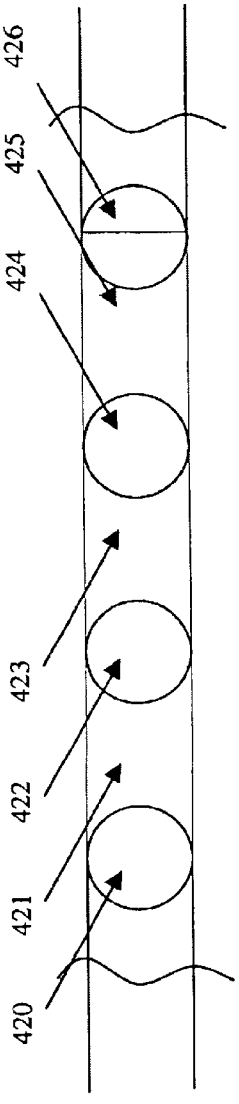

FIGS. 4A–4C provide several embodiments of performing crystallizations within a lumen. It should be recognized that depending upon the differing surface energies of the solutions and the enclosure the actual interfaces may be convex, concave, flat or with elements of all three. For illustrative purposes, the interfaces are shown to be spherical.

FIG. 4A illustrates a crystallization mixture 401 formed within a lumen 403 positioned between two dividers 400, 402. The lumen 403 is formed at least partially by a substrate 407 and enclosed therein.

Generally, dividers may be used according to the present invention to separate aliquots of material within the microvolumes, typically the lumens. The separated aliquots of materials may correspond to separate experiments such as the crystallization trials described herein.

The dividers 400, 402 may be semi-permeable gases or liquids, semi-permeable gels or permeable gels, or thixotropic liquids, or immiscible and impermeable liquids or beads. As a result, the interface formed between a crystallization and a divider may be a liquid/liquid, liquid/gas interface, liquid/solid or liquid/sol-gel interface. In some instances, the interface may also be a membrane, gel, frit, or matrix to modulate or alter the diffusion characteristics.

The dividers can be impermeable, semi-permeable or permeable. For example, semi-permeable substances such as air, oil, solvent, gel and beads can be used as dividers. The dividers can also be physical constructions, such as a narrow pore, a thin passage, a frit or sintered beads or powders.

In one variation, the dividers function to modulate diffusion characteristics between adjacent samples. For example, the one or more dividers may be formed of a semi-permeable material that allows diffusion between adjacent crystallization samples.

In crystallizations performed within lumens according to the present invention, there may be one or multiple crystallization conditions, either related or unrelated in a given lumen. The dividers serve to separate and optionally isolate the different crystallization conditions. For example, a second crystallization condition, potentially one of many, is illustrated by dividers 404, 406 surrounding crystallization 405. The dividers and the gap 403 may optionally be omitted.

Alternatively, the substance to be crystallized can be element 401, with 400 and 402 being crystallization agents, either identical or different. In this instance, element 403 functions as a barrier between one condition and the next. As illustrated in FIG. 4B, element 403 can be omitted for a series of crystallizations.

By positioning barrier material on opposing sides of a crystallization within the microlumen, the crystallization may be encased and its length thereby controlled. Examples of barrier materials that may be used include, but are not limited to immiscible solvents or solids. The barrier materials may form a complete or partial barrier. Complete barriers prevent the crystallization from traversing the barrier material. Partial barriers limit the rate at which components of the crystallization traversing the barrier material. Examples of partial barrier materials include, but are not limited to polymers or solvents that allow for diffusion. Diffusion within the crystal conditions can be further modified by the use of thixotropic agents, gels or sols to prevent convective movements of the solutions.

As an alternative method, the substance to be crystallized may be elements 400, 402, 404, and 406. In this instance, elements 401 and 405 may be crystallizing agents. Element 403 meanwhile may be a barrier or can be another crystallization agent.

In all cases, the crystallization agent can be mixed prior to attempting to perform the crystallization within the lumen or can act in situ, with no prior mixing.

FIG. 4B illustrates a crystallization performed within a lumen where multiple crystallization conditions are simultaneously employed. As illustrated, elements 411, 413, and 415 can be crystallization conditions, either premixed with crystallization agents or not. If elements 411, 413, and 415 are premixed, then elements 410, 412, 414, 416 may optionally be a semi-permeable gas or liquid, a semi-permeable gel or permeable gel, a thixotropic liquid, an immiscible liquid, an impermeable liquid or bead, or a crystallization agent.

In the instance where 411, 413, and 415 are not premixed, then minimally, 412 and 414 are crystallization agents and the termini, 410 and 416 are a barrier (e.g., either a bead, an impermeable substance or a gas bubble).

In the instance that the crystallization is rapid, it is not necessary to have impermeable termini. Instead, diffusion from the termini can be used as an additional crystallization agent.

FIG. 4C illustrates a crystallization performed within a lumen where a series of crystallization agents are set up for crystallization against a series of substances to be crystallized. In FIG. 4C, the crystallization agents are shown as elements 420, 422, 424, and 426. The crystallization attempts comprising substances to be crystallized are shown as elements 421, 423, and 425. These crystallization attempts may or may not be identical.

The sequential crystallizations can be formed in the microlumen by the sequential addition of the materials in inverse order. Thus, sample 406 may be loaded into the microlumen, followed by 405, followed by 404 and so forth. Obviously, the microlumen can be loaded from right to left or left to right. The individual crystallizations may be made on the cassette by using a manifold such as the one show in FIG. 3D, and then varying the relative pressures in the manifold individually or in parallel to achieve the desired mixing. For instance, barrier material might be loaded via 309, protein via 309', semi-permeable material via 309", and a crystallization agent via 309'". The alternating volumes of fluid can be easily made outside of the microlumen by the sequential loading of a syringe pump. To do this, the syringe loads the first sample volume from the source of the first material 400 by creating a pressure differential. The second material 401 is then loaded by the same method. Then the next material 403 is loaded until either the volume limit is reached upon the syringe or the desired contents of the microlumen have been loaded. The syringe pump can then unload the contents into the inlet port on the microlumen.

FIG. 4C might be conveniently constructed through the use of a Tee as shown in FIG. 3A, wherein a series of crystallization conditions could be injected into the microlumen, alternating with suitable injections of material to be crystallized. It will be appreciated by those skilled in the art, that complete droplets can be made by small bursts of differential pressure.

FIGS. 5A–5D illustrate crystallizations being performed within lumens where one or more of the elements of the crystallization experiment change along a length of the lumen. As will be explained, the change can occur discretely or continuously, and need not be changed in a simple linear method.

FIG. 5A illustrates a lumen 501 where the crystallization condition is different across the lumen.

FIG. 5B illustrates a series of substances to be crystallized, shown as elements 510, 511, 512, and 514. These substances are present in a single gradient 513 such that the different elements are exposed to different crystallization conditions.

FIG. 5C illustrates an alternative to the embodiment shown in FIG. 5B. In this embodiment, a series of different crystallization agents 520, 521, 522, and 524 are present within the lumen and are used to provide different conditions for crystallizing substance 523 present across the lumen.

FIG. 5D illustrates diffusion between the various elements in an in situ crystallization. Termini 1 and 7 share a single interface for diffusion. Each of the remaining portions of the in situ crystallization share at least two distinct interfaces for diffusion. Thus, a single substance to be crystallized, present across the lumen, can be assayed against two or more crystallization agents simultaneously. For example, substance 2 is shown to share two separate interfaces, which can cause crystals to grow either near the 1 to 2 interface or the 2 to 3 interface. Crystals growing in the center of 2 are indicative of a substance that requires aspects of both 1 and 3 to crystallize.

The gradient shown in FIG. 5A can be created by using a "Tee" shown in FIG. 3A together with a series of mixing baffles downstream. Initially all of the input flow comes from one of the ports, for example 302". The flow in the second port 302'" is increased, usually with a corresponding decrease in the amount of material flowing in at 302". The relative injection volumes, the total volume injected and the rate at which they change will affect the final gradient produced. Gradients may be formed off chip by similar means. The addition of a series of crystallization agents can be effected via the use of a "Tee" as described above, or may be individually loaded in an inlet port.

FIG. 6A illustrates a crystallization performed within a lumen where a single crystallization condition 601 occupies an entire crystallization space.

FIG. 6B illustrates multiple crystallizations being performed within a lumen where dividers 611, 612, 615, 617 are used between the crystallizations 610, 612, 614, 616, and 618. The dividers are shown in the figure to have planar surfaces adjacent the crystallizations.

FIG. 6C illustrates multiple crystallizations being performed within a lumen where dividers 621, 623, 625 are used between the crystallizations 622, 624. The dividers are shown in the figure to have curved, convex surfaces adjacent the crystallizations 622, and 624 that have complementary concave surfaces. The actual shape of the meniscus dividing the samples is a function of the surface tension at the interface and the surface of the microlumen.

FIG. 7A shows a device for performing a series of crystallizations within a series of lumens where each lumen comprises a loading port 701 and an unloading port 703 and a lumen body 702 interconnecting the ports.

FIG. 7B shows a cross section of a device 700 for performing a crystallization within a lumen where the lumen 702 is not enclosed.

FIG. 7C shows a cross section of a device 700 for performing a crystallization within a lumen where the lumens 702 are rectangular in shape.

FIG. 7D shows a cross section of a device 700 for performing a crystallization within a lumen where the lumens 702 are curved or tubular in shape.

FIG. 7E shows a device for performing crystallizations within a series of lumens where the lumens are loaded with samples 705, 707 that are separated by divider or modifier segments 704, 706, 708. It should be appreciated that each discrete sample may have conditions that are potentially unique and unrelated to adjacent samples. The dividers or modifiers positioned between the samples can be permeable, semi-permeable or impermeable.

The series of crystallizations shown in 7E can be created via the same methods used to create samples 4A above. To expedite the process, it is preferable to load some or all of the channels simultaneously.

FIG. 8A shows a device 800 for performing a series of different crystallizations within a series of lumens where each lumen comprises a loading port 801 and unloading port 803 and a lumen body 802 interconnecting the ports.

FIG. 8B illustrates a single lumen 802 in which a barrier 805 is adjacent to the crystallization condition 806 bounded by second barrier 807. The crystallization conditions can be a larger volume, or the same volume or smaller volume than the barriers. A more complex form of FIG. 8B, is shown in FIG. 8C. It is noted that the barriers used herein correspond to the dividers described above.

FIG. 8C illustrates a diffusion crystallization. The barrier 805', which can be either permeable or impermeable, is adjacent to the crystallization condition 806', which is bounded by the barrier 807', which can be either permeable, semi-permeable and is adjacent to crystallization condition 808', which differs from condition 806' in at least one component Condition 808' is bounded by boundary condition 809', which can be permeable, semi-permeable or impermeable. Conditions 806' and 808 form a set of linked crystallization conditions, whose rate of equilibration is modulated by the properties of barrier 807'. This example can be easily generalized to an entire crystallization channel or plate by suitable construction of the conditions and the plate itself. This is illustrated with regard to FIG. 8D.

FIG. 8D illustrates a multi-component crystallization being performed in a single lumen. The multi-component crystallization consists of end barriers 809 and 839 and crystallization conditions 811 through 837, each separated from its adjacent neighbor conditions by a permeable or semi-permeable barrier 810, repeating along the channel as 810' between each condition 811 through 837. Any number of conditions can be coupled via semi-permeable or permeable barriers depending on the dimensions of the lumen, the design of the plate and crystal arrays and the volumes of the various crystal conditions.

Various methods may be performed using devices that allow for diffusion between adjoining flows within a single lumen. For example, in one embodiment, a microfluidic method is provided that comprises: delivering first and second fluids to a lumen of a microfluidic device such that the first and second fluids flow adjacent to each other within the lumen without mixing except for diffusion at an interface between the first and second fluids, wherein the first fluid is different than the second fluid. In a variation according to this embodiment, the composition of at least one of the first and second fluids is varied over time as it is delivered to the lumen so that the fluid forms a gradient with regard to a concentration of at least one component of the fluid that changes along a length of the lumen. In another variation according to this embodiment, the microfluidic device may comprise a plurality of lumens, the method further comprising delivering first and second fluids to each of the plurality of lumens.

According to this embodiment, the same first and second fluids may be delivered to each of the plurality of lumens. Alternatively, different first and second fluids are delivered to the different lumens of the plurality of lumens. The first and second fluids may also have a same or different flow rate within the lumen.

In another embodiment, a microfluidic method is provided that comprises: delivering first and second fluids to a lumen of a microfluidic device such that the first and second fluids flow adjacent to each other within the lumen without mixing except for diffusion at an interface between the first and second fluids, wherein the first fluid is different than the second fluid and a composition of at least one of the first and second fluids delivered to the lumen is varied so that the composition of at least one of the first and second fluids within the lumen varies along a length of the lumen.

In yet another embodiment, a microfluidic method is provided that comprises: delivering first, second and third fluids to a lumen of a microfluidic device such that the first, second and third fluids flow adjacent to each other within the lumen without mixing except for diffusion at an interface between the first, second and third fluids, wherein the first, second and third fluids are different than each other and a composition of at least one of the first, second and third fluids delivered to the lumen is varied so that the composition of at least one of the first, second, and third fluids within the lumen varies along a length of the lumen.

According to any of these embodiments, the composition of at least one of the first, second and third fluids may be varied over time as it is delivered to the lumen so that the fluid forms a gradient with regard to a concentration of at least one component of the fluid that changes along a length of the lumen. Also according to any of these embodiments, the microfluidic device may comprise a plurality of lumens, the method comprising delivering first, second and third fluids to each of the plurality of lumens. The same or different first, second and third fluids may be delivered to each of the plurality of lumens. Optionally, at least one of the first, second and third fluids have a different flow rate than another of the fluids within the lumen. Also, at least one of the first, second and third fluids may have the same flow rate than another of the fluids within the lumen. Also according to any of these embodiments, the first, second and third fluids may be combined to form different crystallization conditions for crystallizing a molecule such as a protein. In one variation, the first, second and third fluids combine to form different crystallization conditions, the second fluid comprising the material to be crystallized and being positioned between the first and third fluids.

In regard to any of these embodiments, dividers may optionally be used in one or more of the first, second and optionally third or more fluids. These dividers may be used to set up multiple separate aliquots in the fluid flow where the dividers are positioned.

One particular application of these various methods is the use the first, second and optionally third or more fluids to form different crystallization conditions for crystallizing a material such as a protein.

Devices and methods that allow for diffusion between adjoining flows within a single lumen will now be described in regard to FIGS. 9A–9D.

Figure 9A:
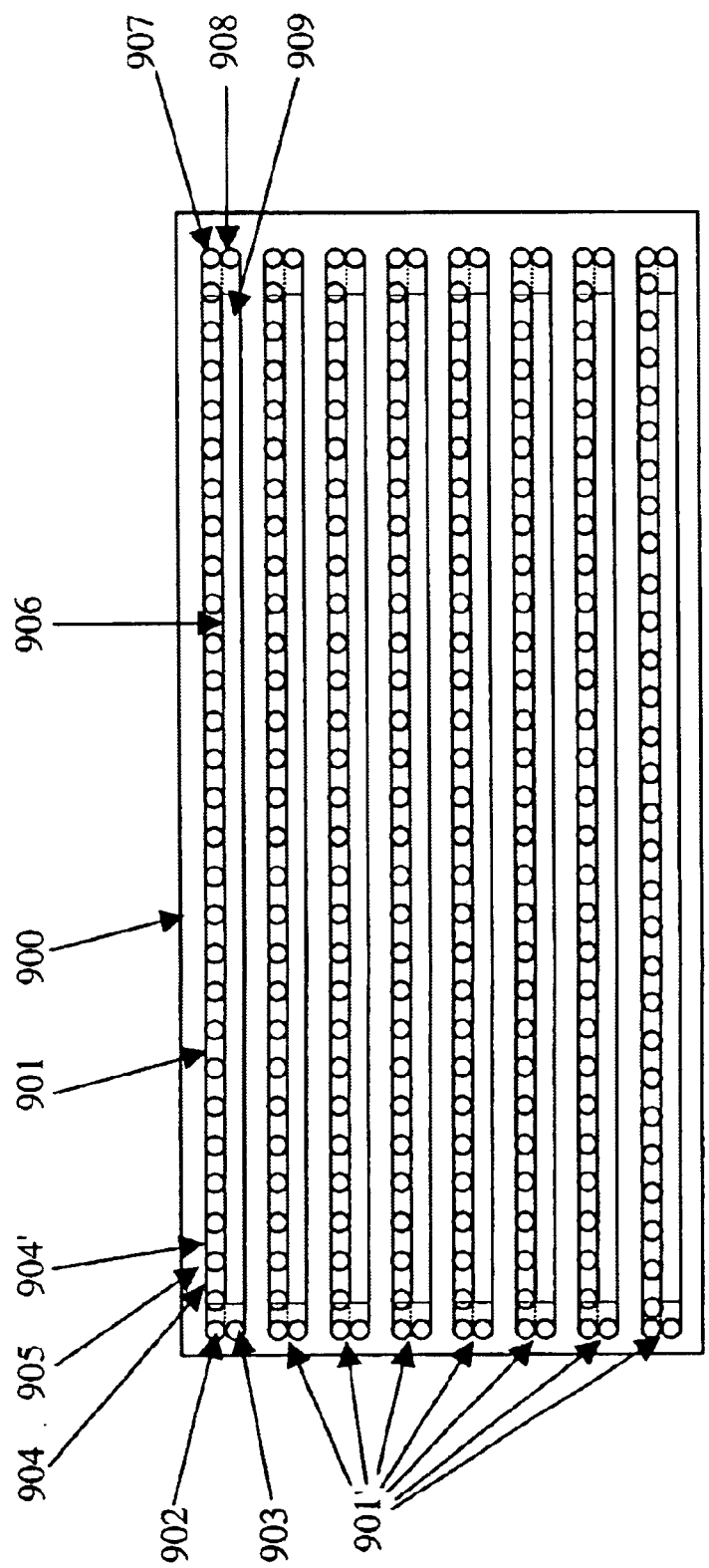
FIG. 9A shows an embodiment of a device for performing a series of different crystallizations within a series of lumens where each lumen comprises a loading and unloading port and a lumen body interconnecting the ports.

FIG. 9A shows an embodiment of a device 900 being used to perform a series of different crystallizations within a series of multi-lumen assemblies 901, 901' where each multi-lumen assembly comprises at least one and preferably two loading 902, 903 and unloading 907, 908 ports and a lumen body 901 interconnecting the ports.

The fluids for each crystallization may be contained in two distinct fluid flows 902, 903 from the port that are in contact with each other along a shared interface 906.

It is noted that this shared interface 906 is not a structure but is an interface that forms between the two distinct fluid flows as a result of laminar flow within a microvolume dimensioned lumen. By contrast, FIGS. 10A–10B describe adjacent fluid flows in separate lumens where a permeable or semi-permeable shared wall is positioned between the lumens that allows for diffusion between fluids in the separate lumens.

The fluid flows consist of a crystallization condition 909 and a series of crystallization conditions 904 and 904' that are separated by a barrier 905, which may be permeable, semi-permeable or impermeable. This arrangement enables the simultaneous examination of many different conditions against a single condition.

The lumen shown in FIG. 9A can be either preloaded with a fluid or not. It is preferable, however, that the pairs of fluid flows be simultaneously loaded via the inlet ports 902 and 903. Having an existing fluid in the lumen may facilitate maintaining the laminar flow necessary to maintain a uniform interface 906 between the two fluid flows.

A method for loading a single channel has been described above. This process can be used to produce the samples introduced via inlet port 902. Simultaneous with the injection of the material via port 902 is the injection of the desired material 909. This method can be easily generalized to more than two fluid flows.

Figure 9B:
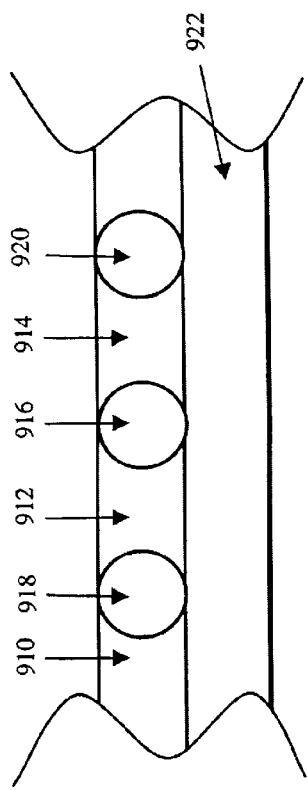
FIG. 9B illustrates an enlargement of a lumen of the device shown in FIG. 9A that illustrates some of the different simultaneous diffusions that are enabled by the invention.
Figure 9C:
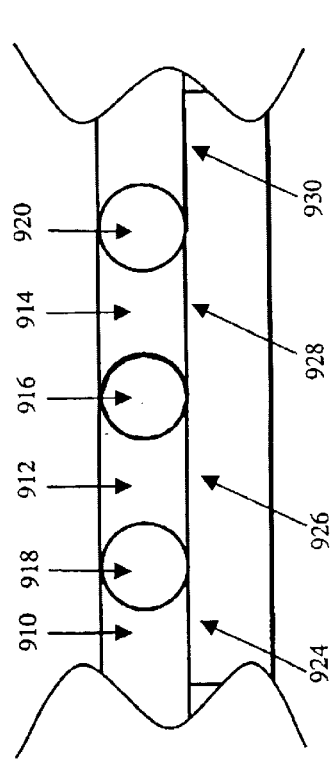
FIG. 9C illustrates the device shown in FIG. 9B where diffusion occurred through the barrier to form a gradient from condition to condition.
Figure 9D:
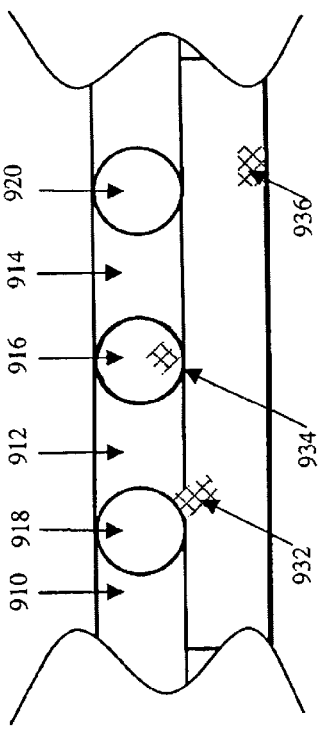
FIG. 9D illustrates crystals forming at different locations after the diffusion shown in FIG. 9C.

FIGS. 9B–9D show an embodiment of a crystallization experiment that may be performed using the device of FIG. 9A.

FIG. 9B illustrates an enlargement of a lumen of the device shown in FIG. 9A which illustrates some of the different simultaneous diffusions that are made possible by the invention. In fluid flow 910, aliquots of crystallization agents 912, 914 are positioned on opposing sides of permeable or semi-permeable barrier 916. Further aliquots may be positioned upstream and downstream of the portion of the flow shown. Barriers 918, 920 on the outer sides of aliquots 912, 914 may be impermeable and thereby isolate these aliquots relative to the remainder of the fluid flow. As shown, barriers 918, 920 are permeable or semipermeable, allowing for diffusion further along fluid flow 910.

As illustrated in FIG. 9C, when the intervening barriers are permeable or semi-permeable, diffusion occurs through the barrier to form a gradient from condition 912 to condition 914. Furthermore, fluid flow 922 adjacent fluid flow 910 also forms a diffusion front between the two flows. As a result, diffusion between fluid flow 922 and aliquots 912, 914 also occurs. These different diffusions are illustrated in FIG. 9C by circles 924, 926, 928 and 930.

As can be seen from FIG. 9C, this method provides for the diffusion of crystallization components longitudinally between differing conditions in a manner that can be regulated through the suitable choice of barriers as well as laterally across an interface formed by the laminar flow of microfluid flows, FIG. 9D illustrates crystals forming at different locations. For example, crystal 932 is shown positioned between the fluid flows and crystal 934 is shown positioned within divider 916. Meanwhile, crystal 936 is shown to be formed on the portion of the diffusion interface farthest from aliquot 914. The positioning of the crystals relative to the aliquots and the fluid flows can be used to indicate which crystallization conditions are conducive and not conducive to crystal formation. As can be seen, the multiplicity of different conditions that may be formed by using these multiple different diffusion fronts allows a great level of diversity of crystallization conditions to be created.

Crystallization conditions can be examined as part of a time series and the time and location of nucleation, initial crystallization or precipitation can be observed or derived. By using known, or observed diffusion rates, the actual conditions at the nucleation or crystallization points can be determined and used for further, more detailed crystallizations. This method thus allows for a finer and more complete examination of crystallization conditions than can be afforded by single condition mixing of crystallization agents and the material to be crystallized.

The diffusions illustrated in FIGS. 9B–9D are based on diffusion between first and second adjacent fluid flows. It should be recognized that this method and device design can be readily extended to three, four, or more adjacent fluid flows.

The diffusions illustrated in FIGS. 9B–9D are also based on multiple aliquots in the first fluid flow. These multiple aliquots may have the same or different composition. They may comprise crystallization agents and/or the material to be crystallized It should be recognized that the second fluid flow may also have multiple aliquots.

Various devices and methods are also provided that allow for diffusion between adjoining lumens. For example, in one embodiment, a microfluidic device is provided that comprises: a substrate; a first lumen at least partially defined by the substrate; and a second lumen; wherein the first and second lumens share a common wall with each other that allows for diffusion between the two lumens over at least a portion of the length of the two lumens.

In another embodiment, a microfluidic device is provided that comprises: a substrate; a plurality of sets of lumens, each set comprising a first lumen at least partially defined by the substrate, and a second lumen, wherein the first and second lumens share a common wall with each other that allows for diffusion between the two lumens over at least a portion of the length of the two lumens.

It is desirable for these devices to allow for a high degree of parallel experimentations. Accordingly, the devices preferably comprise at least 4, 8, 12, 24, 96, 200, 1000 or more sets of lumens with adjoining walls.

According to each embodiment, the common wall may optionally comprise a membrane, gel, frit, or matrix that allows for diffusion between the two lumens.

Also according to each embodiment, the device may further comprise a third lumen, the third lumen sharing a common wall with at least one of the first and second lumens so as to allow for diffusion between the lumens over at least a portion of the length of the lumens.

Microfluidic methods are also provided. For example, in one embodiment, a microfluidic method is provided comprising: delivering a first fluid to a first lumen of a microfluidic device and a second, different fluid to a second lumen of the microfluidic device, the first and second lumens sharing a common wall that allows for diffusion between the lumens over at least a portion of the length of the lumens; and having the first and second fluids diffuse between the first and second lumens.

It is noted in regard to the devices and methods that laminar flow allows for separate fluid flows to be delivered in a same lumen, as discussed above in regard to FIGS. 9A–9D. As a result, it should also be recognized that the common wall need not be present along an entire length of the adjacent lumens. Further, it should be noted that one, two or more separate fluid flows may be added to each lumen.

Devices and methods that allow for diffusion between adjoining lumens will now be described in regard to FIGS. 10A–10B FIG. 10A illustrates an embodiment of a device 1000 being used to perform a series of different crystallizations within a series of multi-lumen assemblies 1001, 1001' where each multi-lumen assembly comprises a first lumen 1002 and a second lumen 1004, the first and second lumens sharing a common wall 1006 that allows for diffusion between the lumens over at least a portion of the length of the lumens. Each lumen has a separate loading 1008, 1010 and unloading 1012, 1014 ports that are each in fluid communication with a lumen.

A separate fluid flow 1016, 1018 is delivered to each lumen through the loading ports 1008, 1010.

It is noted that the common wall 1006 in FIG. 10A differs from the shared interface 906 of FIG. 9A because it is an actual permeable or semi-permeable structure positioned between the lumens that allows for diffusion between fluid in the separate lumens.

FIG. 10B illustrates an alternate embodiment where the multi-lumen assembly comprises a first lumen 1002, a second lumen 1004, and a third lumen 1005 where the first, second and third lumens share common wall 1006, 1007 that allows for diffusion between the lumens over at least a portion of the length of the lumens.

It is noted that a composition of at least one of the first and second fluids may be varied so that the composition of at least one of the first and second fluids varies along a length of the lumen. The composition of at least one of the first and second fluids may also vary over time as it is delivered to the lumen so that the fluid forms a gradient with regard to a concentration of at least one component of the fluid that changes along a length of the lumen. Depending on the experiment, the same or different first and second fluids may be delivered to each of the plurality of first and second lumens.

It is also noted that the first and second fluids may have a same or different flow rate within the lumen.

When a third separate lumen is provided, the method may optionally further comprise delivering a third fluid to a third lumen which shares a common wall with at least one of the first and second lumens, the common wall allowing for diffusion between the third lumen and the first or second lumen over at least a portion of the length of the lumens.

It should be recognized that the embodiments of FIGS. 9A–9D and FIGS. 10A–10B may optionally be combined. For example, a device according to FIG. 10A or 10B may be employed where two or more fluids flows are introduced into a single lumen, as illustrated in FIGS. 9A–9D.

FIGS. 10C–10E show an embodiment of a crystallization experiment that may be performed. Shown in the figures are an enlargement of the double lumen device shown in FIG. 10A. Lumen 1002 is separated from lumen 1004 by the permeable or semi-permeable wall 1006.

In FIG. 10C, lumen 1002 is illustrated as containing a series of crystallization agents 1020, 1020', and 1020". These crystallization agents in lumen 1002 are separated by impermeable dividers 1022' and a semi-permeable divider 1022. This allows separate aliquot to be created in that lumen. It should be recognized that the dividers employed in this embodiment are optional.

Lumen 1004 meanwhile is shown to contain the mixture to be assayed for crystallization, such as a protein solution in a buffer. Once the lumens are filled, diffusion between the differing chemical mixtures begins.

As shown in FIG. 10D, after some time has passed, diffusion can occur both through the semi-permeable internal divider 1022, as well as through the permeable or semi-permeable wall 1006. The chemical gradients from the crystallization agents are illustrated as diffusion fronts 1024, 1026, diffusing into the crystallization mixtures, and as the intra-lumen diffusion from 1021. It is noted that diffusion front 1021 can also permeate through the permeable or semi-permeable wall 1006, resulting in a joint diffusion front 1025.

FIG. 10E illustrates a sample series of crystal growths that have occurred after some diffusion has occurred. Crystal 1028 is in the center of diffusion front 1024 and has resulted largely from the action of crystallization condition 1020'. Crystal 1029 has grown on the diffusion interface 1025 and is therefore indicative of a crystal that needs chemical moieties of both condition 1020' and condition 1020" to form. In contrast, crystal 1030 has formed on the portion of the diffusion interface farthest from condition 1020', suggesting that some aspect of condition 1020' slows or prevents crystal growth in the context of the crystallization agent 1020". As can be seen, the multiplicity of different conditions that may be formed by using these multiple different diffusion fronts allows a great level of diversity of crystallization conditions to be created.

As shown in FIG. 10F, multiple lumens 1002, and 1004 may be separated by permeable or semi-permeable wall 1006. Lumens 1004 and 1005 are separated by permeable or semi-permeable wall 1007. By the suitable loading of crystallization conditions, 1040, 1041, 1042, 1043, 1044, 1045, 1046, 1047, 1048, and 1049, the skilled artisan can produce many well defined opportunities for diffusion between the various conditions. By the design of suitable experiments the diffusion rates of the chemical moieties within crystallization conditions can be determined. Once the diffusion patterns have been established, the location of crystals within the lumen can be used to interpolate the nucleation and crystal growth conditions between the existing conditions.

Figure 11A:
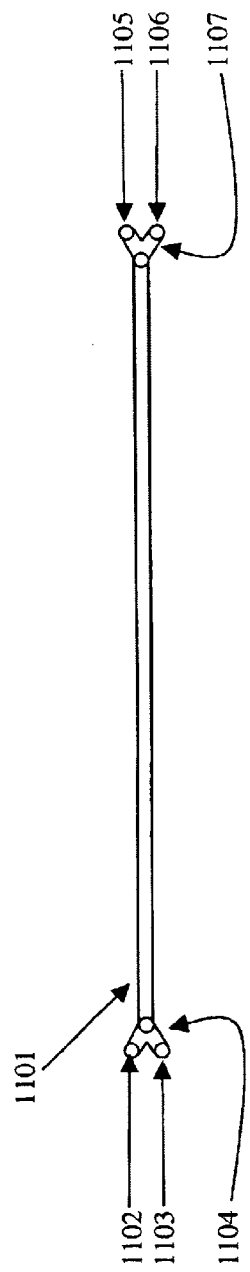
FIG. 11A illustrates a single lumen with integral mixing and harvesting channels.

FIG. 11A illustrates a single lumen with integral mixing and harvesting channels. The single channel comprises an inlet assembly of at least two inlet ports 1102, 1103 and mixing channel 1104, a crystallization channel 1101 and a harvesting assembly 1107, comprised of at least one harvesting port 1105 and preferably two ports 1106 for harvesting.

Figure 11B:
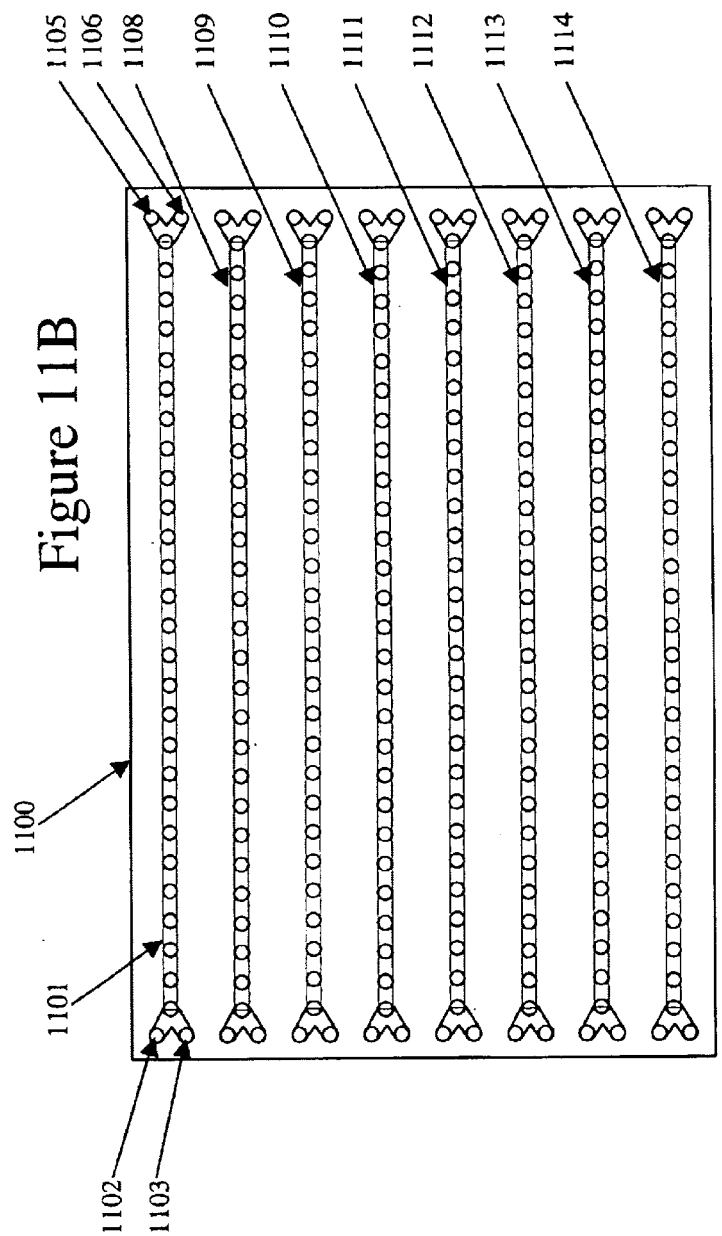
FIG. 11B shows an embodiment of a device for performing a series of different crystallizations within a series of lumens where each lumen comprises integral mixing and harvesting channels.

FIG. 11B shows an embodiment of a device 1100 for performing a series of different crystallizations within a series of lumens 1101, 1108–1114 where each lumen comprises integral mixing and harvesting channels. Conditions with each channel may consist of identical conditions, or of multiple crystallization agents or of multiple substances to be crystallized or any combination thereof.

The "Y" shown in FIGS. 11A and 11B is easily utilized to alternate a series of materials. Syringes or syringe pumps can alternately deliver material to ports 1102 and 1103. Simply, a small interruptible vacuum can be applied to either 1105 or 1106 and the other can be sealed. Alternatively, the vacuum can be applied to both. Whenever a sample is loaded into 1102, port 1103 is sealed and the vacuum is applied at 1105/1106 to transfer the appropriate volume into the "Y" 1104. When the desired volume has been transferred, the pressure differential is removed. Material can then be loaded at 1103, port 1102 is then sealed and a pressure difference sufficient to deliver the required volume into 1104 is applied. The process can then be repeated. For ease of control, it may be preferable to preload the lumens with a hydraulic transfer fluid. Similarly, it is preferable to apply constant pressure difference between the pair 1102/1103 and the pair 1105/1106. The lumen 1101 can then be loaded by alternating the supply of material from 1102 and the supply of material from 1103.

FIG. 12A illustrates a device 1200 comprising a series of lumens, each lumen having attached to it an array of individual crystallization cells 1204, each cell having at least one separate inlet 1202 or outlet 1203 and at least one channel connecting the cell to the lumen 1201. Each crystallization cell may have an exclusive inlet and outlet, giving an array of independent cells, or the cells may be linked, or multiplexed with a common inlet or outlet lumen 1201, which can have a single 1202 or multiple ports 1202, 1205. Substances unique to each crystallization cell are loaded via the port 1203, with the excess being drawn off via the common lumen. Substances common to all cells in a sub-array 1208, consisting of port 1202, manifold 1201, port 1205 and all thus linked crystallization cells and ports, can be loaded through ports 1202 and 1205 by any combination of injection of suction via the ports within the sub-array. By suitable application of driving forces, substances can be driven into any one of the attached crystallization cells, either in parallel or individually.

FIG. 12B illustrates an embodiment of an individual crystallization cell shown in FIG. 12A. If the device is to consist of individually accessed crystallization cells, then port 1201 is unique to each cell. If the cassette includes multiple sub-arrays, then lumen 1201 may be common with the other crystallization cells of the sub-array.

FIG. 12C illustrates an embodiment of an individual crystallization cell 1204 shown in FIG. 12A where the cell comprises a crystallization agent 1207 and a substance 1206 to be crystallized. The exact nature of the meniscus between the substances is highly dependent upon both the sequence of addition of the crystallization materials, their relative volume and the surface properties of the supporting materials of the cassette, e.g. surface energy, hydrophobicity, hydrophilicity, or adsorbed materials.

4. Delivery of Materials To Microsized Lumens

Materials may be added to the devices of the present invention by a variety of different methods and mechanisms. For example, material may be added to a given lumen by the sequential addition of the volumes of materials that need to be added or may be delivered as a single bolus. Commercial robots such as the Staübli can deliver small volumes of material with the high degree of accuracy needed to repeatedly deliver the necessary drops into entry ports of the lumens. For improved accuracy, multiple deliveries can be used to create the final, larger volume, from a series of smaller volumes.

Volume of materials can be delivered by a number of different mechanisms, such as ultrasonic dispensers, peristaltic pumps, syringes, syringe pumps or stepper motor driven plungers Materials can be delivered to multiple different lumens individually, in parallel within a channel, or in parallel across the entire device. For some embodiments, it may be desirable to deliver two or three conditions simultaneously for optimal loading. Alternatively, it is possible to use pin arrays to deliver the fluid.

The device may also be docked with a manifold in order to deliver materials to the lumens of the device. This manifold can be mated with at least one or multiple inlet ports. The channels in the chip can then be filled individually, or in parallel from the manifold. The filling cycle may be entirely in parallel, or the filling cycle may involve multiple docking events. If the device is docked multiple times to different manifolds, the materials can be added by alternately mating the device with, for example, a protein manifold, a barrier manifold, and a crystallization manifold. The materials may be pressure driven into the device, or may be applied with vacuum, or a combination thereof. Under some constructs, it may be advantageous to pre-fill the device with a fluid. This fluid can then be displaced by the pressure addition of material, or this fluid may be removed actively be an applied vacuum, or a combination thereof to deliver the necessary fluids. Pre-filling the device has advantages in the fluidics, and also for the alteration or modulation of the surface properties of the lumen.

5. Transport in Microfluidic Devices Using Centrifugal Force

One feature of the present invention relates to the use of centrifugal force to cause material to flow within the microlumens of devices according to the present invention. Through the use of centrifugal force, fluids can be loaded, measured, filtered, mixed and incubated within a lumen. The centrifugal force serves to generate hydrostatic pressure to drive the fluids through the lumens, reservoirs, filters and manifolds. This method has the advantages of speed, tightly enclosed fluids to minimize evaporation, and simplicity since there are no moving parts on the device to break or become fouled through the application of external energies. The use of centrifugal force is compatible with a wide variety of fluids.

Optionally, the centrifugal forces are applied such that at least 0.01 g, 0.1, 1 g, 10 g, 100 g or more force is applied to the material in the device to cause the material to move within the microvolumes.

Applying the centrifugal forces may be performed by rotating the device. Optionally, the centrifugal forces are applied by rotating the device at least 10 rpm, 50 rpm, 100 rpm or more. It is noted that the rotational axis about which the microfluidic device is rotated may be positioned within or outside the lateral footprint of the microfluidic device.

A particular advantage of the use of centrifugal force is the ability to make hundreds to thousands to hundreds of thousands of replicate volume measurements simultaneously. Accordingly, devices may be designed so that material in at least 4, 8, 12, 36, 96, 200, 1000 or more different microvolumes are transported when centrifugal force is applied.

In addition, since a common amount of force can be applied to each lumen and the shapes of the lumens can be closely controlled, replicate volume measurements can be made with a high degree of reproducibility. For example, devices can be designed so that the volume of fluid delivered from in a given microvolume upon the application of centrifugal force is within 50%, 25%, 10%, 5%, 2%, 1% or less of the volume of fluid delivered in any other microvolumes.

A further feature of the use of a device employing centrifugal force is the ability to preload crystallization agents. This can be used to dramatically enhance the speed and efficiency of the crystallization setup.

In one embodiment, a microfluidic method is provided that comprises: taking a microfluidic device comprising a plurality of microvolumes; and causing movement of material in a same manner within the plurality of microvolumes by applying centrifugal forces to the material.

In another embodiment, a microfluidic method is provided that comprises: taking a plurality of microfluidic devices, each device comprising a plurality of microvolumes; and causing movement of material in a same manner within the plurality of microvolumes of the plurality of devices by applying centrifugal forces to the material.

In a variation, the plurality of microfluidic devices may be stacked relative to each other when the centrifugal forces are applied. The plurality of microfluidic devices may also be positioned about a rotational axis about which the plurality of microfluidic devices are rotated to apply the centrifugal forces.

In another embodiment, a microfluidic method is provided that comprises: taking a microfluidic device comprising a plurality of microvolumes; and physically moving the device so as to effect a same movement of material within the plurality of microvolumes. Physically moving the device preferably causes centrifugal force to be applied, for example, by rotation of the device about an axis. According to this embodiment, the material moved in each of the plurality of microvolumes by movement of the device preferably has a same quantity.

In another embodiment, a microfluidic method is provided that comprises: taking a microfluidic device comprising a plurality of microvolumes; and accelerating or decelerating a motion of the device so as to effect a same movement of material within the plurality of microvolumes. According to this embodiment, the motion of the device is optionally a rotation of the device. In such instances, acceleration or deceleration may be caused by a change in a rate of rotation of the device.

In another embodiment, a microfluidic device is provided that comprises: a substrate; and a plurality of microvolumes at least partially defined by the substrate, each microvolume comprising a first submicrovolume and a second submicrovolume that is in fluid communication with the first submicrovolume when the device is rotated, the plurality of microvolumes being arranged in the device such that fluid in the first submicrovolumes of multiple of the microvolumes are transported to second submicrovolumes of the associated microvolumes when the device is rotated.

In yet another embodiment, a microfluidic device is provided that comprises: a substrate shaped so as to provide the device with an axis of rotation about which the device may be rotated; and a plurality of microvolumes at least partially defined by the substrate, each microvolume comprising a first submicrovolume and a second submicrovolume that is in fluid communication with the first submicrovolume when the device is rotated, the plurality of microvolumes being arranged in the device such that fluid in the first submicrovolumes of multiple of the microvolumes are transported to the second submicrovolumes of the associated microvolumes when the device is rotated about the rotational axis. Optionally, the second microvolumes are lumens.

The device may optionally comprise a mechanism that facilitates the device being rotated about the rotational axis. For example, the substrate may define a groove or hole at the rotational axis that facilitates the device being rotated about the rotational axis. Optionally, a center of mass of the device is at the rotational axis and the substrate defines a groove or hole at the rotational axis that facilitates the device being rotated about the rotational axis. In one variation, the device is disc shaped, the substrate defining a groove or hole at the rotational axis of the disc that facilitates the device being rotated about the rotational axis.

In another embodiment, a microfluidic method is provided that comprises: taking a microfluidic device comprising a substrate, and a plurality of microvolumes at least partially defined by the substrate, each microvolume comprising a first submicrovolume and a second submicrovolume where the first submicrovolume and second microvolume are in fluid communication with each other when the device is rotated; adding fluid to a plurality of the first submicrovolumes; and rotating the device to cause fluid from the plurality of first submicrovolumes to be transferred to the second submicrovolumes in fluid communication with the first submicrovolumes.

In another embodiment, a microfluidic method is provided that comprises: taking a plurality of microfluidic devices, each comprising a substrate, and a plurality of microvolumes at least partially defined by the substrate, each sample microvolume comprising a first submicrovolume and a second submicrovolume where the first submicrovolume and second submicrovolume are in fluid communication with each other when the device is rotated; adding fluid to a plurality of the first submicrovolumes in the plurality of microfluidic devices; and rotating the plurality of microfluidic devices at the same time to cause fluid from the plurality of first submicrovolumes to be transferred to the second submicrovolumes in fluid communication with the first submicrovolumes.

In another embodiment, a microfluidic method is provided that comprises: taking a microfluidic device comprising a substrate, and a plurality of microvolumes at least partially defined by the substrate, each microvolume comprising a first and a second submicrovolume where the first and second submicrovolumes are in fluid communication with each other when the device is rotated about a rotational axis of the device; adding fluid to a plurality of the first submicrovolumes; and rotating the device about the rotational axis of the device to cause fluid in the first submicrovolumes to be transferred to the second submicrovolumes.

In another embodiment, a microfluidic device is provided that comprises: a substrate; one or more microvolumes at least partially defined by the substrate, each microvolume comprising a first submicrovolume, a second submicrovolume where fluid in the first submicrovolume is transported to the second submicrovolume when the device is rotated about a first rotational axis, and a third submicrovolume where fluid in the first submicrovolume is transported to the third submicrovolume when the device is rotated about a second, different rotational axis.

In another embodiment, a microfluidic device comprising: a substrate; one or more microvolumes extending along a plane of the substrate, each microvolume comprising a first submicrovolume, a second submicrovolume where fluid in the first submicrovolume is transported to the second submicrovolume when the device is rotated about a first rotational axis that is positioned further away from the second submicrovolume than the first submicrovolume, and a third submicrovolume where fluid in the first submicrovolume is transported to the third submicrovolume when the device is rotated about a second, different rotational axis that is positioned further away from the third submicrovolume than the first submicrovolume.

In another embodiment, a microfluidic method is provided that comprises: taking a microfluidic device comprising a substrate and a plurality of microvolumes at least partially defined by the substrate, each microvolume comprising an first submicrovolume, a second submicrovolume where fluid in the first submicrovolume is transported to the second submicrovolume when the device is rotated about a first rotational axis, and a third submicrovolume where fluid in the first submicrovolume is transported to the third submicrovolume when the device is rotated about a second, different rotational axis; adding fluid to the first submicrovolumes of the microvolumes; and in any order rotating the device about the first and second rotational axes to cause fluid from the first submicrovolumes to be transferred to the second and third submicrovolumes.

In another embodiment, a microfluidic device is provided that comprises: a substrate; and a plurality of microvolumes at least partially defined by the substrate, each microvolume comprising a first submicrovolume and a second submicrovolume in fluid communication with the first submicrovolume when the device is rotated about a first rotational axis, wherein rotation of the device about the first rotational axis causes a fixed volume to be transported to each of the second submicrovolumes.

According to this embodiment, the plurality of microvolumes may optionally further comprise one or more outlet submicrovolumes in fluid communication with the first submicrovolume.

Also according to this embodiment, the plurality of microvolumes may optionally further comprise one or more outlet submicrovolumes where fluid in the first submicrovolume not transported to the second submicrovolume when the device is rotated about a first rotational axis is transported to one or more one or more outlet submicrovolumes when the device is rotated about a second, different rotational axis.

In another embodiment, a microfluidic device is provided that comprises: a substrate; a first microvolume at least partially defined by the substrate comprising a first submicrovolume; a second submicrovolume where fluid in the first submicrovolume is transported to the second submicrovolume when the device is rotated about a first rotational axis; and a second microvolume at least partially defined by the substrate comprising a third submicrovolume; a fourth submicrovolume where fluid in the third submicrovolume is transported to the fourth submicrovolume when the device is rotated about the first rotational axis; and wherein fluid in the second and fourth submicrovolumes are transported to a fifth submicrovolume where the second and fourth submicrovolumes are mixed when the device is rotated about a second, different rotational axis.

According to this embodiment, the fifth submicrovolume may optionally be in fluid communication with the second and fourth submicrovolumes via the first and third submicrovolumes respectively.

Also according to this embodiment, the device may further comprise one or more outlet submicrovolumes in fluid communication with the first and third submicrovolumes.

Also according to this embodiment, the device may further comprise one or more outlet submicrovolumes in fluid communication with the first and second submicrovolumes where fluid in the first and third submicrovolumes not transported to the second and fourth submicrovolumes when the device is rotated about the first rotational axis is transported to one or more one or more outlet submicrovolumes when the device is rotated about a third, different rotational axis.

In yet another embodiment, a microfluidic method is provided that comprises: taking a microfluidic device comprising a substrate, and a plurality of microvolumes at least partially defined by the substrate, each microvolume comprising a first submicrovolume and a second submicrovolume in fluid communication with the first submicrovolume; adding fluids to the first submicrovolumes; and applying a centrifugal force to the device to cause a same volume of fluid to be transported to the second microvolumes from the first submicrovolumes.

Optionally, the microvolumes may further comprise an outlet submicrovolume in fluid communication with the first submicrovolumes. In such instances, the method may further comprise transporting fluid in the first submicrovolume to the outlet submicrovolume that was not transported to the second submicrovolume when the centrifugal force was applied. The method may also further comprise transporting fluid in the first submicrovolume to the outlet submicrovolume that was not transported to the second submicrovolume when the device is rotated about a first rotational axis by rotating the device about a second, different rotational axis.

In another embodiment, a microfluidic method is provided that comprises: taking a microfluidic device comprising a substrate, a first microvolume at least partially defined by the substrate comprising a first submicrovolume and a second submicrovolume where fluid in the first submicrovolume is transported to the second submicrovolume when the device is rotated about a first rotational axis, and a second microvolume at least partially defined by the substrate comprising a third submicrovolume and a fourth submicrovolume where fluid in the third submicrovolume is transported to the fourth submicrovolume when the device is rotated about the first rotational axis, the microvolumes further comprising a fifth submicrovolume where fluid in the second and fourth submicrovolumes are mixed when the device is rotated about a second, different rotational axis; adding a first fluid to the first submicrovolume and a second fluid to the third submicrovolume; rotating the device about the first rotational axis to transport the first and second fluids to the second and fourth submicrovolumes; and rotating the device about the second rotational axis to transport the first and second fluids from the second and fourth submicrovolumes to the fifth submicrovolume.

In one variation, the fifth submicrovolume is in fluid communication with the second and fourth submicrovolumes via the first and third submicrovolumes respectively.

Optionally, the method further comprises removing fluid from the first and third submicrovolumes that is not transported to the second and fourth submicrovolumes prior to rotating the device about the second rotational axis.

More specific examples of devices and methods according to these numerous embodiments will now be described in relation to the figures.

Figure 13:
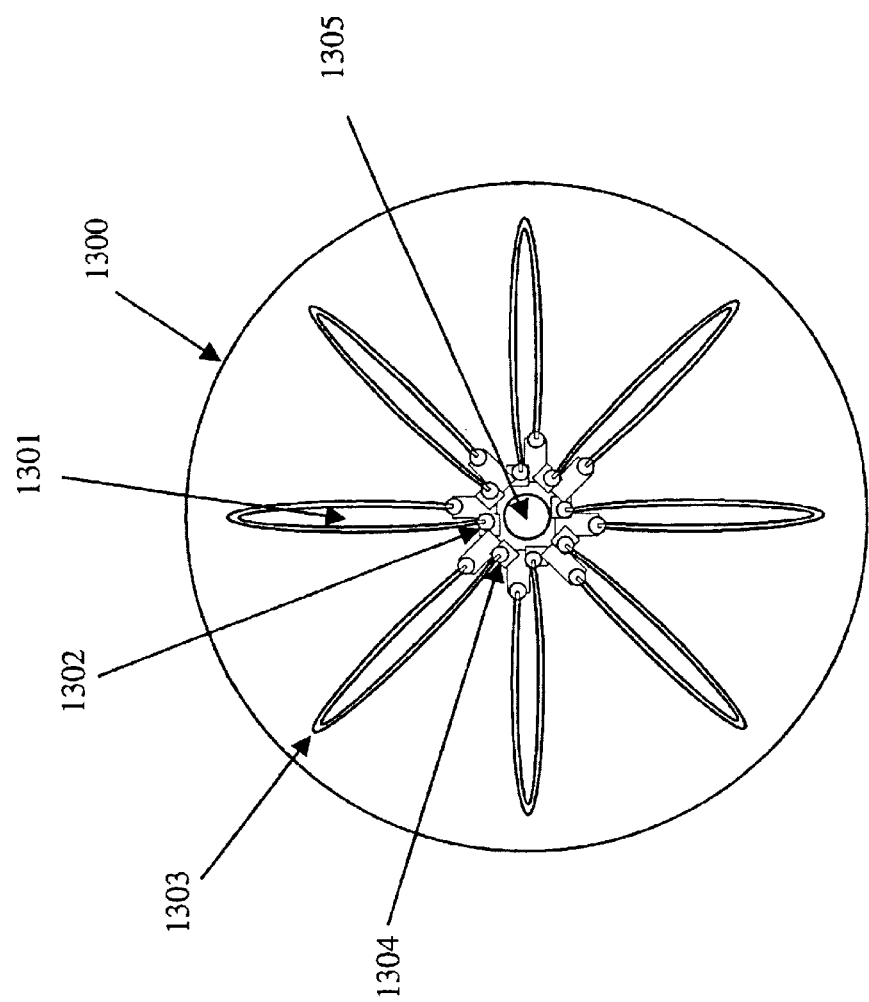
FIG. 13 illustrates a device for forming crystallizations by rotation of the device.

FIG. 13A illustrates a device for forming crystallizations by rotation of the device, thereby applying centrifugal force. The device 1300 comprises multiple crystallization wells 1301, each having at least one inlet port 1302, a crystallization channel 1303 and an outlet port 1304. It is understood that during centrifugation, the radially outermost port will, due to centrifugal forces be the outlet port. However, for the purposes of loading the cassette, either port 1302, 1304 may be used as an inlet or outlet port. The device can have a centering device 1305 to center the device during centrifugation, or alternatively, the device may be inserted in a receiver designed to mate with the device.

As can be seen, the device is similar in design to a compact disc, comprising a flat, circular plate of substrate with a hole in the middle, preferably at the center of mass of the device. Incorporated into the substrate is an array of crystallization chambers. This design allows the crystallization agents to be added to the device. Then, when the device is rotated, the crystallization agents in the different chambers are each caused to enter a corresponding crystallization well.

Given the symmetry of the design and the uniformity of the centrifugal force that is applied, the design of the device provides for a compact system where crystallization agents can be first added and stored in the device. Then, when the device is ready to be used, the device can be rotated to cause the prior added crystallization agents to move within the device. As illustrated in FIG. 13A, the rotational axis about which the microfluidic device is rotated may be within a lateral footprint of the device.

The design of the device also allows for multiple devices to be stacked upon each other. This allows for a great number of devices to be processed in parallel. FIG. 13B illustrates a plurality of the devices shown in FIG. 13A where the devices are stacked relative to each other when the centrifugal forces are applied so that the same forces are applied to all of the devices.

Figure 14:
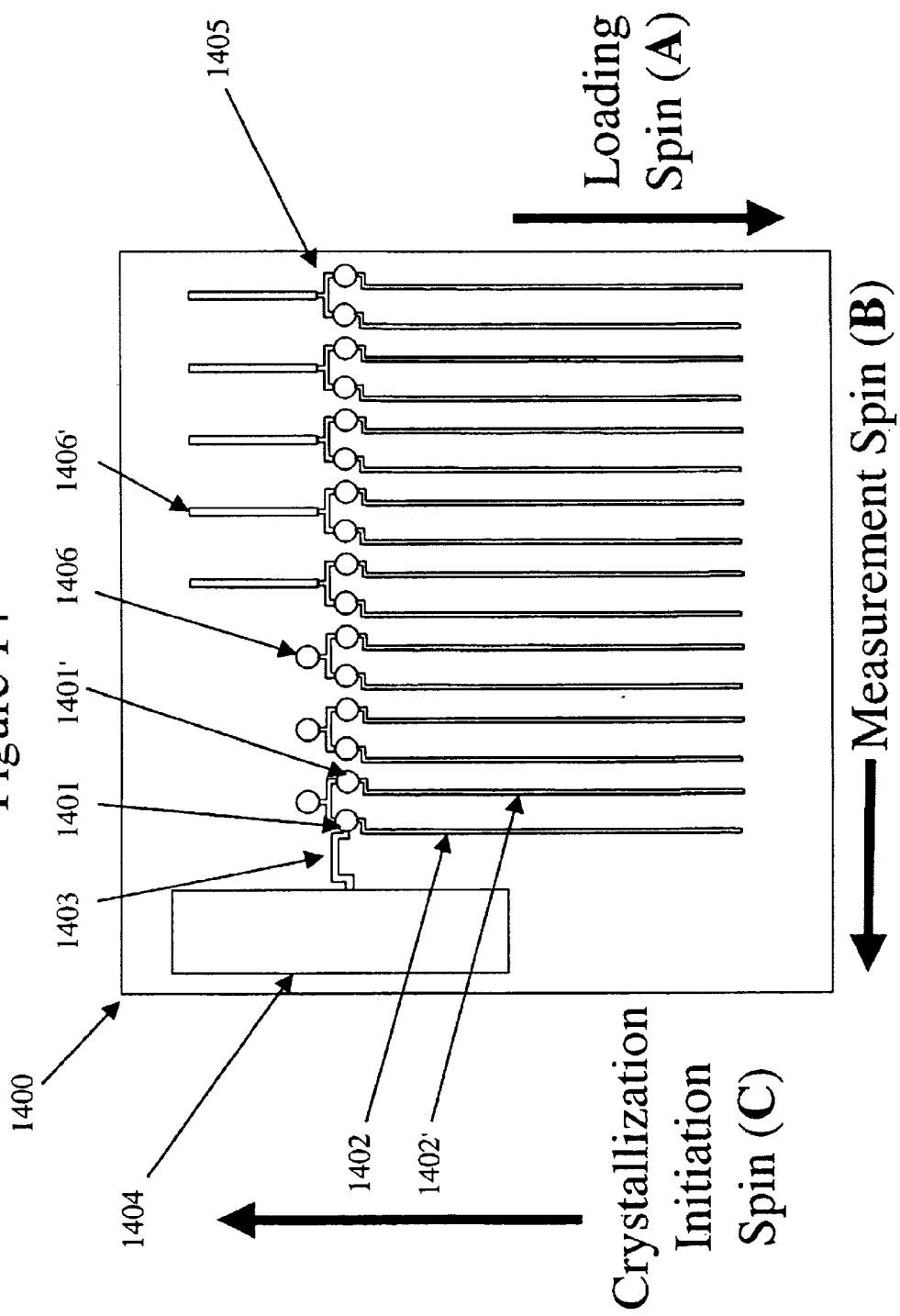
FIG. 14 illustrates a device that is designed to move fluids within the device by centrifugal force.

FIG. 14A illustrates another embodiment of a device 1400 that is designed to move fluids within the device by centrifugal force. This design allows for the precise measurement of very small volumes without the use of moving parts, electromotive force or active pumps within the device. The device consists of at least two inlet chambers 1401, 1401', a measurement channel 1402 for each inlet, a waste channel 1403 from each inlet 1401 to a waste reservoir 1404 or outlet, a mixing manifold 1405 connecting the measurement channels 1402, 1402' and the crystallization chamber 1406. The manifold, can encompass the inlet port, or by pass it. The measurement channels can be of identical or differing volumes, dependent upon the need. The crystallization chamber can be of any shape, shown here as either circular 1406 or rectangular 1406'. Only one waste channel is illustrated, but each measurement channel has an associated waste channel. These channels can be independent, or by suitable design can form a manifold.

The device may be employed as follows; into each inlet chamber 1401, a volume of crystallization agent or substance to be crystallized is added. The volume that is added does not need to be precise or accurate. Instead, it is sufficient that the volume is greater than a minimum volume for the measurement channel 1402. The crystallization agents can be dispensed in advance of the substance to be crystallized, enabling the device to be made in advance and used as needed. Once the inlet chambers are all filled, the device is rotated with the centrifugal force vector approximately aligned as shown, for the loading spin (A).

The centrifugal force fills the measurement channel 1402 completely, leaving some residue in the inlet chamber 1401. A subsequent measurement spin (B), removes the excess from the inlet chamber and deposits the excess in the waste reservoir 1404 or port, leaving the inlet chamber empty. At this point, the device may be stored until needed. The inlet ports may be sealed by the application of a tape, lid, septum, or by stacking the devices together.

The rotational axis about which the microfluidic device illustrated in FIG. 14A is rotated is positioned further away from the measurement channel 1402 than the inlet chamber 1401. This provides the centrifugal force vector the directionality that is shown during the loading spin (A). The rotational axis about which the microfluidic device is rotated may be within or outside of the lateral footprint of the device.

The substance to be crystallized is then added into each inlet chamber 1401'. The volume does not need to be precise or accurate. Instead, it is sufficient that the volume be greater than a certain minimum for the measurement channel 1402'. Once the inlet chambers are all filled, the device is centrifuged with the centrifugal force vector as shown, for the loading spin (A). This fills the measurement channel 1402' completely, leaving some residue in the inlet chamber 1401'.

A subsequent measurement spin (B) with the centrifugal force vector approximately in this direction, removes the excess from the inlet chamber and deposits the excess in the waste reservoir 1404 or port, leaving the inlet chamber empty. At this point, the device may again be stored until needed. The inlet ports may be sealed by the application of a tape, lid, septum, or by stacking the plates together.

It is noted that the rotational axis about which the microfluidic device is rotated in the subsequent measurement spin (B) is positioned in a different location than the rotational axis during the load spin (A). In this instance, the different rotational axes are laterally offset relative to each other. The rotational axis for the measurement spin (B) is also positioned her away from the waste reservoir 1404 or port than the inlet chamber 1401. This positioning causes the centrifugal force vector to be in the direction illustrated in regard to the measurement spin (B). It is noted that the rotational axis about which the microfluidic device is rotated during the measurement spin may also be within or outside of the lateral footprint of the device. Although the rotational axes are shown to be parallel and laterally offset relative to each other, it should be recognized that the axes may also be angled relative to each other. Crystallization, or the test of crystallization is initiated by centrifugation with the centrifugal force vector approximately in the direction of the crystallization initiation spin (C). This drives the crystallization agent or agents and the substance to be crystallized through a mixing manifold 1405 into a crystallization chamber 1406.

It is noted that the rotational axis about which the microfluidic device is rotated during the crystallization initiation spin (C) is positioned in a different location than during the load spin (A) or the measurement spin (B). For example, the rotational axis for the crystallization initiation spin (C) is positioned further away from the inlet chamber 1401 than the measurement channel 1402. This positioning causes the centrifugal force vector to be in the direction illustrated in regard to the load spin (C), which in this case is in the opposite direction than the centrifugal force vector for the load spin (A). It is again noted that the rotational axis about which the microfluidic device is rotated during the load spin may also be within or outside of the lateral footprint of the device.

The process illustrated in FIG. 14A is an example of a microfluidic method that is provided by the present invention that comprises: taking a microfluidic device comprising a substrate and a plurality of microvolumes at least partially defined by the substrate, each microvolume comprising an first submicrovolume, a second submicrovolume where fluid in the first submicrovolume is transported to the second submicrovolume when the device is rotated about a first rotational axis, and a third submicrovolume where fluid in the first submicrovolume is transported to the third submicrovolume when the device is rotated about a second, different rotational axis; adding fluid to the first submicrovolumes of the microvolumes; and in any order rotating the device about the first and second rotational axes to cause fluid from the first submicrovolumes to be transferred to the second and third submicrovolumes.

FIG. 14B illustrates how multiple devices, such as the device shown in FIG. 14A may be processed together. As illustrated, the multiple devices may be positioned radially about a rotational axis. During each different load, measurement, and initiation spins, each device may be positioned relative to the rotational axis so that the corresponding vector is extending radially away from the rotational axis. It should be noted that the multiple devices may alternatively or in addition be stacked relative to each other, as illustrated in FIG. 13B.

It is noted in regard to the various embodiments involving centrifugal force, such as the embodiment shown in FIG. 14A, that acceleration and deceleration, created by a change in a rate of rotation of the device, can be used. In particular, when a device is rotating and the rate of change of rotation of the device is zero or close to zero, then the primary component of the force vector is radial. However, when the device is initially at a constant rotational speed, which could be zero, and then as the rotational speed of the device is increased, the primary component is initially orthogonal to the radius, and in the rotational plane, tangential to the rotation. This is also true if the device is decelerated. It is also noted that the faster the device is accelerated, the larger the magnitude of the force.

This fact can be used to modulate the flow of liquid within the microfluidic device. A large tangential force vector as the device is being accelerated causes the liquid within device to initially begin flowing in the counter to the direction of the initial force. Thus, the inertial response of the fluid to the centripetal acceleration is to appear to lag the acceleration of the device. Similarly, if the device is decelerated, the fluid will lag the deceleration.

This enables the production of devices that have different fluid behavior depending upon the direction of rotation and the rate of acceleration or deceleration.

In one example, described in relation to the device illustrated in FIG. 14A, if the initial loading spin has a rotational axis on a side of the device adjacent the crystallization chamber 1406 and the device is rapidly accelerated clockwise, fluid placed in loading port 1401 will flow into chamber 1402. Conversely, if the device is initially rotated counter-clockwise with a rapid acceleration, the initial force upon the liquid will direct the liquid largely toward port 1403 and hence to the waste chamber 1404. If the device is accelerated slowly, the primary component of the force vector acting upon the liquid will be radial and the liquid will flow from the loading port 1401 into the chamber 1402, regardless of the direction of rotation. Skilled artisans will appreciate that by suitable design of the substrate and by manipulation of the rate of change of the rotational speed, the fluid flow in the device can be modulated to achieve very different outcomes. It will be understood by those skilled in the art that when the centrifugal force is neither parallel to nor normal to the plane of the device, additional asymmetries in fluid flow may be exploited for more complex fluid partitioning and combinations.

Figure 15A:
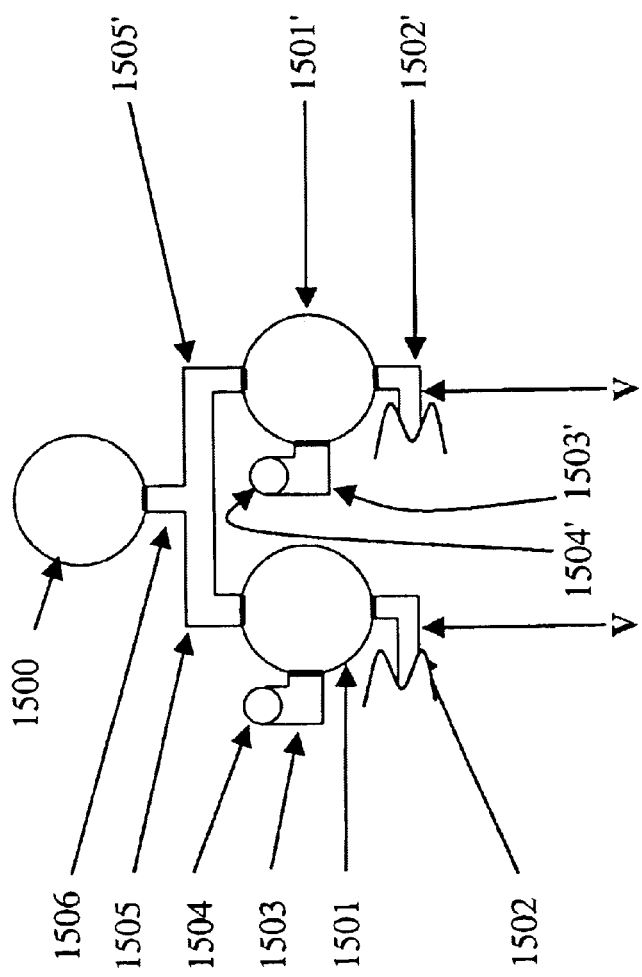

FIG. 15A illustrates how centrifugal force can be used to perform precise measurements. FIG. 15A illustrates a repeating unit of the centrifugal array in more detail. In this embodiment, one inlet for crystallization agents 1501 and one inlet for a substance to be crystallized 1501' are shown. Note that the lumens 1502, 1502' connecting to the measurement lumens have a short neck near the inlet chamber, orthogonal to the measurement spin. V represents the measured volume after the measurement spin. During the measurement spin, excess material in the inlet chamber, and the excess above V is centrifugally ejected through lumens 1503, 1503' and hence through lumens 1504, 1504' to the exit port or reservoir. Note that lumens 1503, 1503', also have a narrow neck, initially oriented parallel to and in the opposite direction to the loading spin vector, ensuring that the liquids proceed down 1502 or 1502' to the measurement lumens.

FIG. 15A thus illustrates a microfluidic method that comprises: taking a microfluidic device comprising a substrate, and a plurality of microvolumes at least partially defined by the substrate, each microvolume comprising a first submicrovolume and a second submicrovolume in fluid communication with the first submicrovolume; adding fluids to the first submicrovolumes; and applying a centrifugal force to the device to cause a same volume of fluid to be transported to the second microvolumes from the first submicrovolumes.

FIG. 15A thus also illustrates an embodiment of a microfluidic device that comprises: a substrate; and a plurality of microvolumes at least partially defined by the substrate, each microvolume comprising a first submicrovolume and a second submicrovolume in fluid communication with the first submicrovolume when the device is rotated about a first rotational axis, wherein rotation of the device about the first rotational axis causes a fixed volume to be transported to each of the second submicrovolumes.

As illustrated, the plurality of microvolumes may optionally further comprise one or more outlet submicrovolumes where fluid in the first submicrovolume not transported to the second submicrovolume when the device is rotated about a first rotational axis is transported to one or more one or more outlet submicrovolumes when the device is rotated about a second, different rotational axis. When the microvolumes farther comprise an outlet submicrovolume in fluid communication with the first submicrovolumes, the method may further comprise transporting fluid in the first submicrovolume to the outlet submicrovolume that was not transported to the second submicrovolume when the centrifugal force was applied. The method may also further comprise transporting fluid in the first submicrovolume to the outlet submicrovolume that was not transported to the second submicrovolume when the device is rotated about a first rotational axis by rotating the device about a second, different rotational axis.

FIGS. 15B–15G illustrate how centrifugal force can be used to perform precise measurements and mixing. More specifically, these figures illustrate a microfluidic device that comprises: a substrate; a first microvolume at least partially defined by the substrate comprising a first submicrovolume; a second submicrovolume where fluid in the first submicrovolume is transported to the second submicrovolume when the device is rotated about a first rotational axis; and a second microvolume at least partially defined by the substrate comprising a third submicrovolume; a fourth submicrovolume where fluid in the third submicrovolume is transported to the fourth submicrovolume when the device is rotated about the first rotational axis; and wherein fluid in the second and fourth submicrovolumes are transported to a fifth submicrovolume where the second and fourth submicrovolumes are mixed when the device is rotated about a second, different rotational axis. As will be illustrated, the fifth submicrovolume may optionally be in fluid communication with the second and fourth submicrovolumes via the first and third submicrovolumes respectively. As will also be illustrated, the device may further comprise one or more outlet submicrovolumes in fluid communication with the first and third submicrovolumes. As will also be illustrated, the device may further comprise one or more outlet submicrovolumes in fluid communication with the first and second submicrovolumes where fluid in the first and third submicrovolumes not transported to the second and fourth submicrovolumes when the device is rotated about the first rotational axis is transported to one or more one or more outlet submicrovolumes when the device is rotated about a third, different rotational axis.

FIGS. 15B–15G also illustrate a method that comprises: taking a microfluidic device comprising a substrate, a first microvolume at least partially defined by the substrate comprising a first submicrovolume and a second submicrovolume where fluid in the first submicrovolume is transported to the second submicrovolume when the device is rotated about a first rotational axis, and a second microvolume at least partially defined by the substrate comprising a third submicrovolume and a fourth submicrovolume where fluid in the third submicrovolume is transported to the fourth submicrovolume when the device is rotated about the first rotational axis, the microvolumes further comprising a fifth submicrovolume where fluid in the second and fourth submicrovolumes are mixed when the device is rotated about a second, different rotational axis; adding a first fluid to the first submicrovolume and a second fluid to the third submicrovolume; rotating the device about the first rotational axis to transport the first and second fluids to the second and fourth submicrovolumes; and rotating the device about the second rotational axis to transport the first and second fluids from the second and fourth submicrovolumes to the fifth submicrovolume.

It is noted that different sets and subsets of combinations described herein can be performed without departing from the present invention.

Figure 15B:
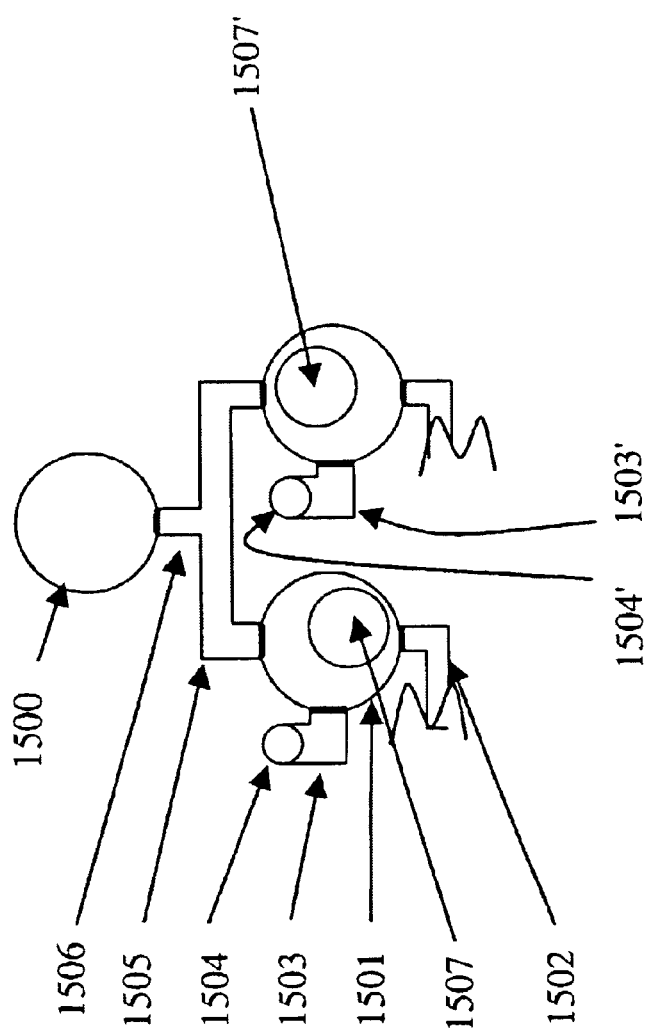

Referring to FIG. 15B a device is shown where a crystallization agent 1507 has been added into the entry port, or well 1501. Also shown is the material to be crystallized 1507' in a second entry port or well. These materials need not be added contemporaneously.

FIG. 15C illustrates the effect of centrifugal force on the samples that were loaded to the device in FIG. 15B. Upon the application of centrifugal force, the bulk of the material 1507 and 1507' proceeds to fill the respective measurement lumens 1502 and 1502'. This leaves some amount of excess material 1508 and 1508' in the initial loading wells 1501 and 1501', respectively.

Figure 15D:
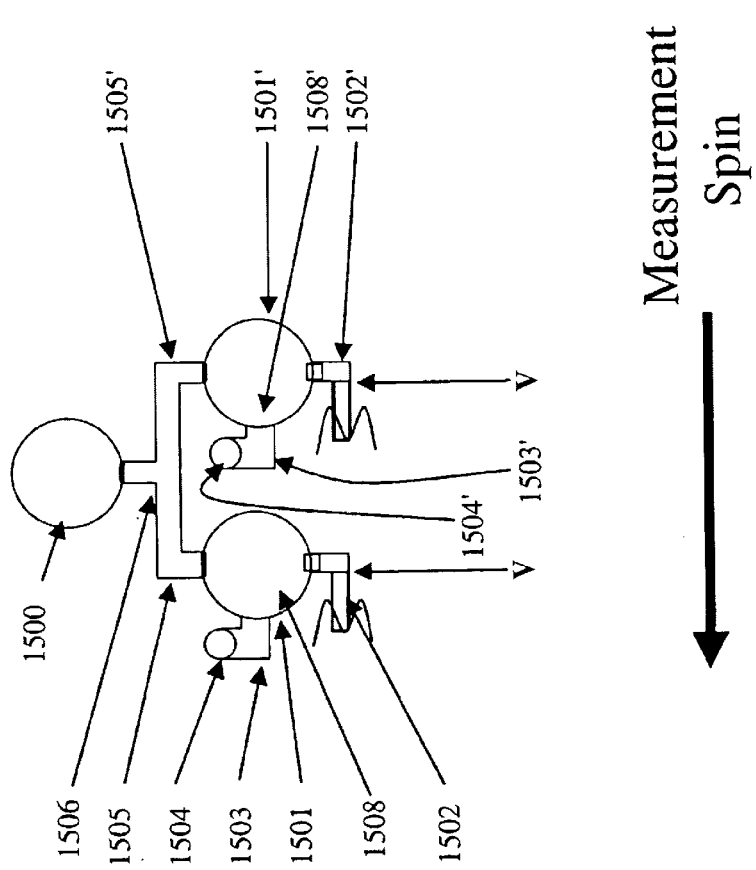

In FIG. 15D, the centrifugal force vector is changed such that the force now directs the excess crystallization agent and excess material to be crystallized 1508 and 1508' toward the waste ports 1504, 1504' via the respective waste lumens 1503, 1503'. After applying this centrifugal force, the measurement channel is filled with material to the point V in every measurement lumen.

Figure 15E:
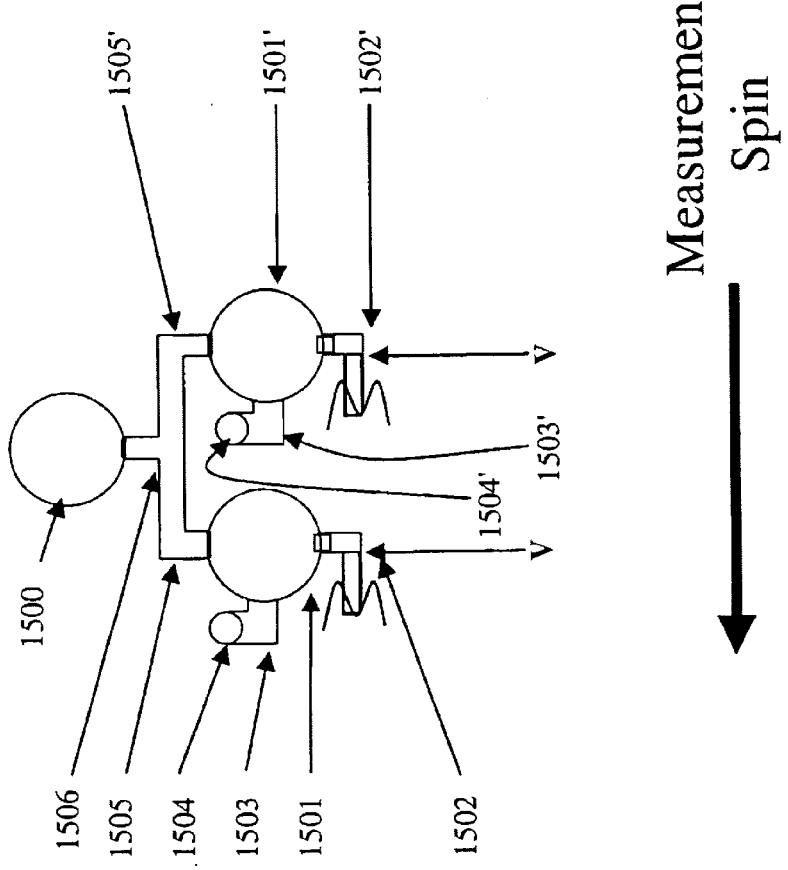

FIG. 15E shows each lumen filled to point V, resulting in precise volume measurements.

Figure 15F:
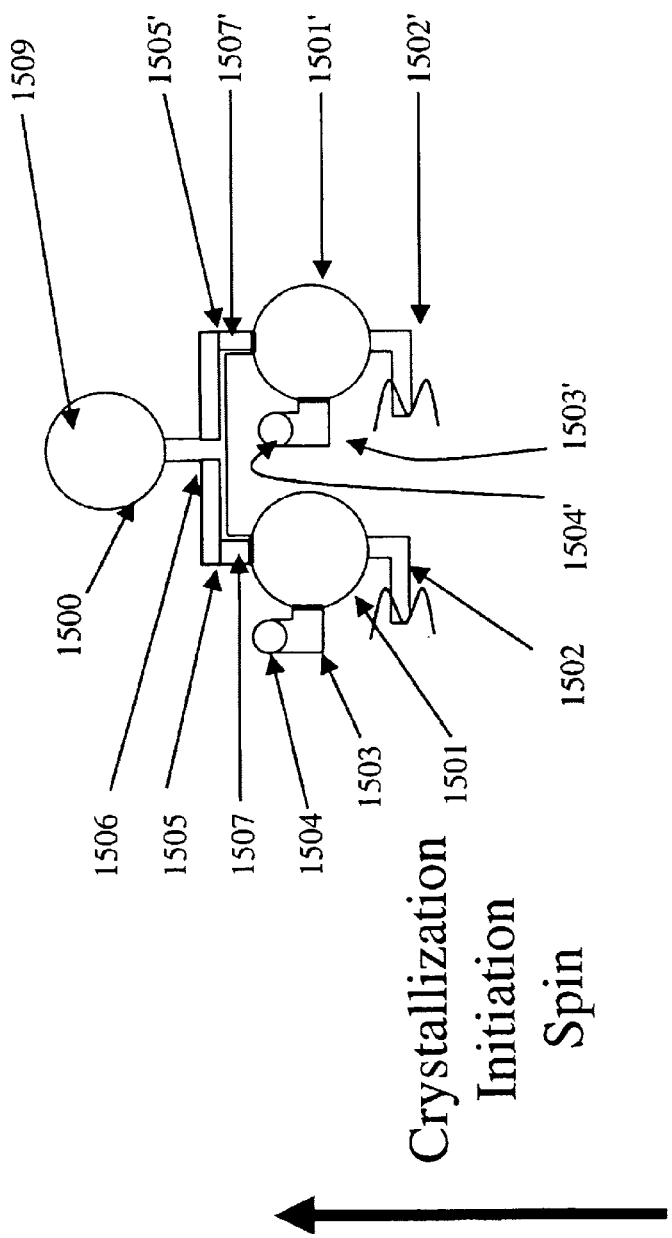

In FIG. 15F, the centrifugal force vector is again changed to align in the direction shown. Centrifugal force in this direction drives the crystallization agent 1507 and the material to be crystallized 1507' from the measurement lumens 1502, 1502', across the inlet ports 1501, 1501' and through a manifold 1505, 1505' to the mixing manifold 1506 and hence into the crystallization chamber 1500, as the mixed material 1509.

Figure 15G:
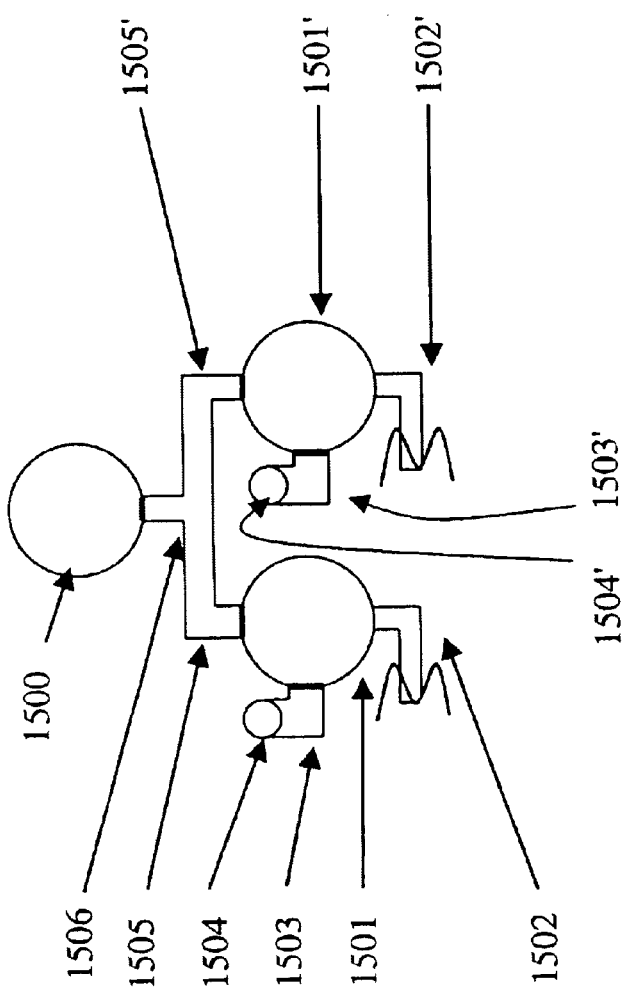

FIG. 15G illustrates the final result, where the crystallization chamber 1500 has been filled with the combination of the material to be crystallized and the crystallization agent, or agents.

As will be appreciated, the process of making precise microfluidic measurements and precise mixing by using centrifugal force can be performed in a highly parallel manner, both by incorporating numerous microvolumes into a given device, and by applying centrifugal force to multiple different devices at the same time, wherein the variations in acceleration, or deceleration, will be uniformly applied over all devices and all lumens within said devices.

6. Use of the Devices of the Present Invention To Determine Crystal Growth Conditions One of the intended uses of the devices of the present invention is for improving the process of discovering novel crystal growth conditions. By using the devices of the present invention, a simultaneous, multiple factor approach can be implemented.

Current methods of vapor diffusion, hanging drop, sitting drop and dialysis evaluate a single test condition in each instance. By contrast, the present invention allows for multiple different crystallization conditions to be created in the same lumen, thereby allowing for multiple different crystallization conditions to be tested. In some embodiments, gradients are created which create the multiple different crystallization conditions. Diffusion of either the sample being evaluated and/or the enclosing medium having a viscosity such that the diffusion of the chemical moieties for crystallization is much faster than the diffusion of bulk material allows for the gradients to be created. This can be achieved either through intrinsically viscous materials or additives such as agarose, acrylamide, silica gel, or PEG, or by the use of filter plugs, or by the use of enclosing channels that are sufficiently thin in at least one dimension to limit macroscopic flow such that diffusion of the chemical moieties for crystallization dominate. These samples can be affected by sample droplets in a channel, droplets within an enclosing crystallization medium, or crystallization droplets or islands within an enclosing volume of sample.

While the present invention is disclosed with reference to preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. The patents, papers, and books cited in this application are to be incorporated herein in their entirety.

We claim:

1. A microfluidic method comprising:
   delivering a first fluid to a first lumen of a microfluidic device and a second, different fluid to a second lumen of the microfluidic device, the first and second lumens sharing a common wall which allows for diffusion between the lumens over at least a portion of the length of the lumens; and
   having the first and second fluids diffuse between the first and second lumens.

2. A microfluidic method according to claim 1 wherein a composition of at least one of the first and second fluids is varied so that the composition of at least one of the first and second fluids varies along a length of the lumen.

3. A microfluidic method according to claim 1 wherein the composition of at least one of the first and second fluids varies over time as it is delivered to the lumen so that the fluid forms a gradient with regard to a concentration of at least one component of the fluid that changes along a length of the lumen.

4. A microfluidic method according to claim 1 wherein the microfluidic device comprises a plurality of first and second lumens, the method comprising delivering first and second fluids to each of the plurality of first and second lumens.

5. A microfluidic method according to claim 1 wherein the same first and second fluids are delivered to each of the plurality of first and second lumens.

6. A microfluidic method according to claim 1 wherein different first and second fluids are delivered to the plurality of first and second lumens.

7. A microfluidic method according to claim 1 wherein each lumen has a cross sectional diameter of less than 2.5 mm.

8. A microfluidic method according to claim 1 wherein each lumen has a cross sectional diameter of less than 1 mm.

9. A microfluidic method according to claim 1 wherein each lumen has a cross sectional diameter of less than 500 microns.

10. A microfluidic method according to claim 1 wherein the first and second fluids combine to form different crystallization conditions for crystallizing a molecule.

11. A microfluidic method according to claim 1 wherein the first and second fluids combine to form different crystallization conditions for crystallizing a protein.

12. A microfluidic method according to claim 1 wherein the first and second fluids combine to form different crystallization conditions for crystallizing a macromolecule with a molecular weight of at least 500 daltons.

13. A microfluidic method according to claim 1 wherein the first and second fluids combine to form different crystallization conditions for crystallizing a member selected from the group consisting of viruses, proteins, peptides, nucleosides, nucleotides, ribonucleic acids, deoxyribonucleic acids.

14. A microfluidic method according to claim 1 wherein the first and second fluids have a same flow rate within the lumen.

15. A microfluidic method according to claim 1 wherein the first and second fluids have a different flow rate within the lumen.

16. A microfluidic method according to claim 1 wherein the method further comprises delivering a third fluid to a third lumen which shares a common wall with at least one of the first and second lumens, the common wall allowing for diffusion between the third lumen and the first or second lumen over at least a portion of the length of the lumens.

17. A microfluidic device comprising:
   a substrate;
   a first lumen at least partially defined by the substrate; and
   a second lumen;
   wherein the first and second lumens share a common wall with each other that allows for diffusion between the two lumens over at least a portion of the length of the two lumens.

18. A microfluidic device according to claim 17 wherein the common wall comprises a membrane, gel, frit, or matrix that allows for diffusion between the two lumens.

19. A microfluidic device according to claim 17 wherein each lumen has a cross sectional diameter of less than 2.5 mm.

20. A microfluidic device according to claim 17 wherein each lumen has a cross sectional diameter of less than 1 mm.

21. A microfluidic device according to claim 17 wherein each lumen has a cross sectional diameter of less than 500 microns.

22. A microfluidic device according to claim 17 wherein the device further comprises a third lumen, the third lumen sharing a common wall with at least one of the first and second lumens so as to allow for diffusion between the lumens over at least a portion of the length of the lumens.

23. A microfluidic device comprising:
   a substrate;
   a plurality of sets of lumens, each set comprising
      a first lumen at least partially defined by the substrate, and
      a second lumen,
      wherein the first and second lumens share a common wall with each other that allows for diffusion between the two lumens over at least a portion of the length of the two lumens.

24. A microfluidic device according to claim 23 wherein the common wall comprises a membrane, gel, frit, or matrix that allows for diffusion between the two lumens.

25. A microfluidic device according to claim 23 wherein each lumen has a cross sectional diameter of less than 2.5 mm.

26. A microfluidic device according to claim 23 wherein each lumen has a cross sectional diameter of less than 1 mm.

27. A microfluidic device according to claim 23 wherein each lumen has a cross sectional diameter of less than 500 microns.

28. A microfluidic device according to claim 23 wherein the device further comprises a third lumen, the third lumen sharing a common wall with at least one of the first and second lumens so as to allow for diffusion between the lumens over at least a portion of the length of the lumens.

29. A microfluidic device according to claim 23 wherein the device comprises at least 4 sets of lumens.

30. A microfluidic device according to claim 23 wherein the device comprises at least 8 sets of lumens.

31. A microfluidic device according to claim 23 wherein the device comprises at least 12 sets of lumens.

32. A microfluidic device according to claim 23 wherein the device comprises at least 24 sets of lumens.

33. A microfluidic device according to claim 23 wherein the device comprises at least 96 sets of lumens.

34. A microfluidic device according to claim 23 wherein the device comprises at least 200 sets of lumens.

* * * * *